United States Patent [19]

Hefner, Jr. et al.

[11] Patent Number: 5,248,757
[45] Date of Patent: Sep. 28, 1993

[54] MESOGENIC CYANATE FUNCTIONAL MALEIMIDES AND THERMOSETS THEREOF

[75] Inventors: Robert E. Hefner, Jr.; Jimmy D. Earls, both of Lake Jackson, Tex.

[73] Assignee: The Dow Chemical Company, Midland, Mich.

[21] Appl. No.: 909,919

[22] Filed: Jul. 7, 1992

Related U.S. Application Data

[60] Continuation-in-part of Ser. No. 730,403, Jul. 16, 1991, abandoned, which is a division of Ser. No. 596,138, Oct. 11, 1990, Pat. No. 5,077,380, which is a continuation-in-part of Ser. No. 380,936, Jul. 17, 1989, abandoned.

[51] Int. Cl.$^5$ .................. C08F 22/40; C08G 73/12
[52] U.S. Cl. ............................... 528/322; 525/540; 526/262; 526/285; 526/286; 526/312; 528/116; 528/117; 528/118; 528/119; 528/121; 528/122; 528/190; 528/192; 528/205; 528/211; 528/271; 528/391; 528/392; 528/422
[58] Field of Search .............. 528/322, 116, 117, 118, 528/119, 121, 122, 190, 192, 205, 211, 391, 392, 422, 271; 526/262, 312, 285, 286; 525/540

[56] References Cited

U.S. PATENT DOCUMENTS

| | | | |
|---|---|---|---|
| 4,110,364 | 8/1978 | Gaku et al. | 528/170 |
| 4,287,014 | 9/1981 | Gaku et al. | 156/306.9 |
| 4,330,669 | 5/1982 | Ikeguchi et al. | 528/289 |
| 4,369,304 | 1/1983 | Gaku et al. | 528/322 |
| 4,370,467 | 1/1983 | Gaku et al. | 528/322 |
| 4,371,689 | 2/1983 | Gaku et al. | 528/162 |
| 4,373,086 | 2/1983 | Ikeguchi | 528/322 |
| 4,383,903 | 5/1983 | Ayano et al. | 204/159.16 |
| 4,393,195 | 7/1983 | Gaku et al. | 528/361 |
| 4,396,745 | 8/1983 | Ikeguchi | 525/374 |
| 4,404,330 | 9/1983 | Ikeguchi | 525/374 |
| 4,469,859 | 9/1984 | Gaku et al. | 528/159 |
| 4,680,378 | 7/1987 | Hefner, Jr. | 528/322 |
| 4,683,276 | 7/1987 | Hefner, Jr. | 526/262 |
| 4,731,426 | 3/1988 | Hefner, Jr. | 526/262 |
| 4,749,760 | 6/1988 | Wang | 525/471 |
| 4,769,440 | 9/1988 | Hefner, Jr. | 528/322 |
| 5,106,937 | 4/1992 | Yamaya et al. | 528/322 |

*Primary Examiner*—John Kight, III
*Assistant Examiner*—John M. Cooney, Jr.

[57] ABSTRACT

Compounds containing at least one cyanate group, at least one maleimide group and at least one rodlike mesogenic moiety are prepared by reacting one or more aminophenols containing one or more rodlike mesogenic moieties with a stoichiometric quantity of a maleic anhydride per amine group of said aminophenol and then cyanating the resulting phenolic functional maleimide.

3 Claims, No Drawings

MESOGENIC CYANATE FUNCTIONAL MALEIMIDES AND THERMOSETS THEREOF

CROSS-REFERENCE TO RELATED APPLICATIONS

This application is a continuation-in-part of application serial no. 07/730,403 filed Jul. 16, 1991 (now abandoned) which is a division of application serial no. 07/596,138 filed Oct. 11, 1990 (now U.S. Pat. No. 5,077,380 issued Dec. 31, 1991) which is is a continuation-in-part of application serial no. 07/380,936 filed Jul. 17, 1989 (now abandoned) all of which are incorporated herein by reference in their entirety.

FIELD OF THE INVENTION

The present invention concerns cyanate functional maleimides containing one or more rodlike mesogenic moieties.

BACKGROUND OF THE INVENTION

Copolymerization products of compounds containing two or more cyanate groups with compounds containing two or more maleimide groups are known, for example, from U.S. Pat. Nos. 4,110,364; 4,287,014; 4,369,304; 4,370,467; 4,371,689; 4,373,086; 4,383,903; 4,393,195; 4,396,745; 4,404,330 and 4,469,859. Representative of said copolymerization products is the bismaleimide-triazine resin prepared by copolymerization of bisphenol A dicyanate and N,N'-(methylene-diphenylene)bismaleimide. Preparation of said copolymerization products always requires premixing or contacting together two separate components: the polycyanate compound and the polymaleimide compound.

Hefner, Jr. in U.S. Pat. Nos. 4,680,378; 4,683,276; 4,731,426 and 4,769,440 provides novel compositions which simultaneously contain both a cyanate group and a maleimide group. Thus, said compositions avoid the premixing or contacting together of separate polycyanate and maleimide components to provide products containing cyanate group and maleimide group copolymerization structures.

The novel compositions of the present invention also simultaneously contain both a cyanate group and a maleimide group but additionally contain one or more rodlike mesogenic moieties. The presence of one or more rodlike mesogenic moieties serves to improve one or more physical or mechanical properties of the cured compositions relative to the cured compositions prepared using the cyanate functional maleimides of the prior art.

SUMMARY OF THE INVENTION

The present invention pertains to cyanate functional maleimide compositions containing one or more rodlike mesogenic moieties, particularly those represented by the following Formulas I, II, III or IV

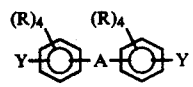

Formula I

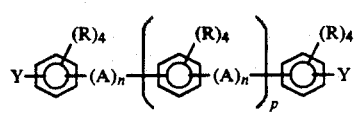

Formula II

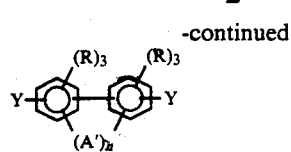

Formula III

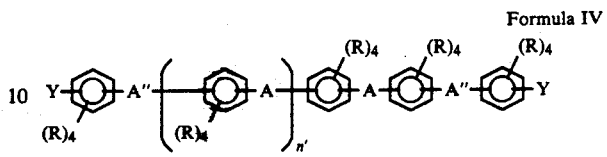

Formula IV wherein at least about 80 percent of the —A— linkages in Formulas I, II and IV and the direct bond in Formula III and the Y groups are in the para position with respect to each other; one Y group is a cyanate, —O—C≡N, group and the other Y group is a maleimide group represented by the formula

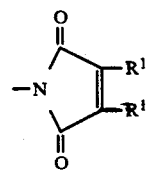

each A is independently —CR$^1$=CR$^1$—, —C≡C—, —N=N—, —CR$^1$=N—, —O—CO—, —NR$^1$—CO—, —CR$^1$=N—N=CR$^1$—, —CR$^1$=CR$^1$—CO—, —CO—O—, —CO—NR$^1$—, —CO—CR$^1$=CR$^1$—, —CR$^1$=CR$^1$—O—CO—(CH$_2$)$_{n'}$—, —N=CR$^1$—, —(CH$_2$)$_{n'}$—CO—O—CR$^1$=CR$^1$—, —CR$^1$—CR$^1$—O—CO—, —CO—O—CR$^1$=CR$^1$—, —CO—O—N=CR$^1$—, —CR$^1$=N—O—CO—, —CR$^1$=CR$^1$—CO—O—, —CO—S—, —O—CO—CR$^1$=CR$^1$—, —CR$^1$=CR$^1$—CO—O—(CH$_2$)$_{n'}$—, —S—CO—, —(CH$_2$)$_{n'}$—O—CO—CR$^1$=CR$^1$—, —CHR$^1$—CHR$^1$—CO—O—, —O—CO—CHR$^1$—CHR$^1$—, —C≡C—C≡C—, —CR$^1$=CR$^1$—CR$^1$=CR$^1$—, —CO—NR$^1$—NR$^1$—CO—,

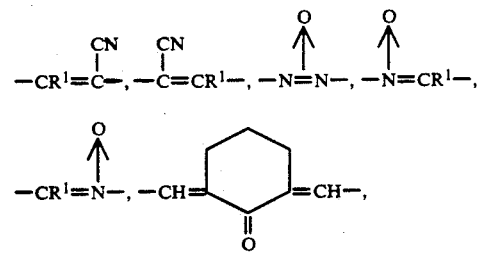

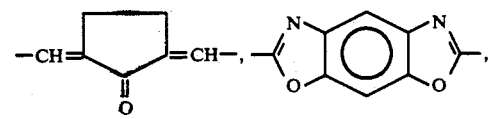

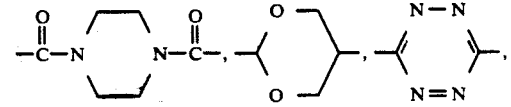

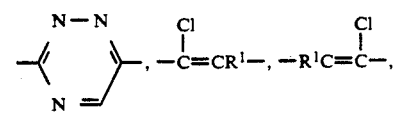

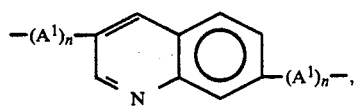

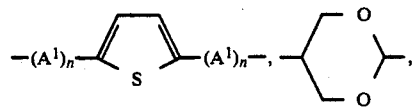

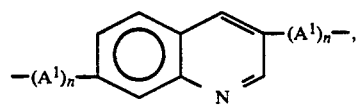

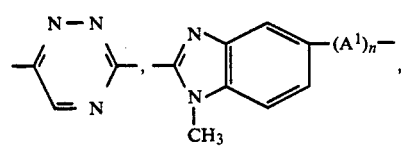

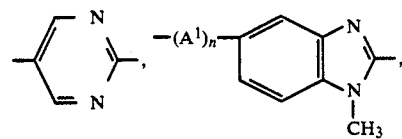

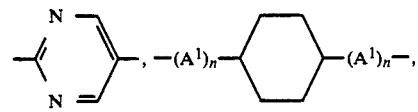

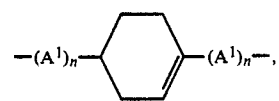

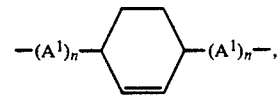

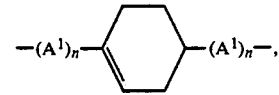

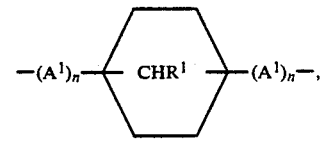

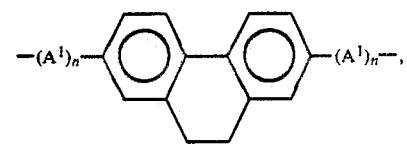

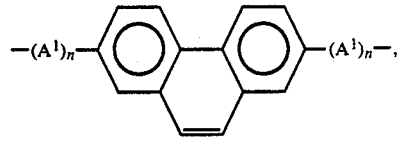

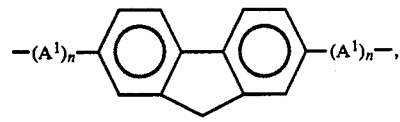

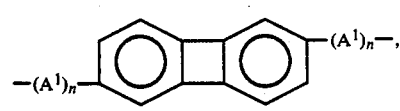

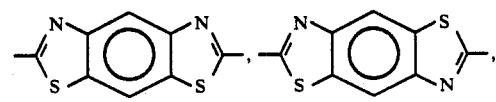

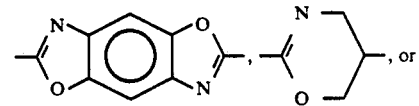

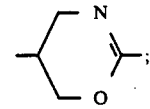

A' is a divalent hydrocarbyl group having from 1 to about 10, preferably from 1 to about 4, carbon atoms; each A" is independently an alkylene group having from 1 to about 10 carbon atoms, preferably from 1 to about 4 carbon atoms, a direct bond, —O—, —CO—, —S—, —S—S—, —SO—, —SO$_2$— or —O—CO—O—; each A$^1$ is independently a —CO—, —O—CO—, —CO—O—, —CO—NR$^1$—, or —NR$^1$—CO— group; each R is independently hydrogen or a hydrocarbyl or hydrocarbyloxy group having from 1 to about 10, preferably from 1 to about 4. carbon atoms, a halogen atom, preferably chlorine or bromine, a nitro group, a nitrile group, a phenyl group or a —CO—R$^1$ group; each R$^1$ is independently hydrogen or a hydrocarbyl group having 1 to about 3 carbon atoms; n has a value of zero or one; n' has an average value from zero to about 6, preferably zero to about 3; and p has an average value from 1 to about 30, preferably from 1 to about 3. The aromatic rings can also contain one or more heteroatoms selected from N, O, S and the like.

Another aspect of the present invention pertains to compositions resulting from curing (thermosetting) one or more of the cyanate functional maleimides containing one or more rodlike mesogenic moieties, optionally in the presence of one or more curing agents or curing catalysts.

Another aspect of the present invention is directed to polymerizable compositions comprising a mixture containing (A) at least one thermosettable cyanate functional maleimide containing one or more rodlike mesogenic moieties; and (B) at least one of (1) at least one polycyanate or polycyanamide which does not contain rodlike mesogenic structures;
(2) at least one epoxy resin;
(3) at least one polymaleimide;
(4) at least one polyamine;
(5) at least one polyphenol;
(6) at least one compound containing one or more polymerizable ethylenically unsaturated group(s);
(7) at least one compound which contains in the same molecule both a cyanate or cyanamide group and a polymerizable ethylenically unsaturated group;
(8) at least one compound which contains in the same molecule both a 1,2-epoxide group and a polymerizable ethylenically unsaturated group;
(9) at least one compound which contains in the same molecule both a maleimide group and a cyanate group and does not contain rodlike mesogenic structures;
(10) at least one compound which contains one or more rodlike mesogenic moieties and only one cyanate or cyanamide group per molecule;
(11) at least one prepolymer of any of the aforesaid components (1) through (10) or any combination of any two or more of said components; or
(12) a mixture of any two or more of components (1) through (11) in any proportion and any combination.

Another aspect of the present invention pertains to compositions resulting from polymerizing the aforementioned polymerizable compositions.

A further aspect of the present invention pertains to products resulting from orienting any of the aforementioned polymerizable compositions.

The term prepolymers as employed herein means that the compound has been homooligomerized or cooligomerized or interoligomerized or homopolymerized or copolymerized or interpolymerized so as to cause an increase in molecular weight, but not to such an extent that the product has become cured, i.e. insoluble and infusible, but rather, the product is capable of being subsequently cured to an insoluble, infusible state.

DETAILED DESCRIPTION OF THE INVENTION

Preparation of the Cyanate Functional Maleimides Containing One or More Rodlike Mesogenic Moieties The cyanate functional maleimides of the present invention are prepared by reacting one or more aminophenols containing one or more rodlike mesogenic moieties with a stoichiometric quantity of a maleic anhydride per amine group of said aminophenol in the presence of a suitable solvent and then cyanating the resulting phenolic functional maleimide.

Suitable aminophenols which can be employed herein to prepare the cyanate functional maleimides containing one or more rodlike mesogenic moieties include, for example, any compound which has an average of one aromatic hydroxyl group and aromatic primary amino group per molecule and include, for example, those represented by the Formulas V, VI, VII or VIII

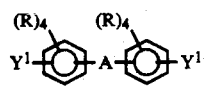

Formula V

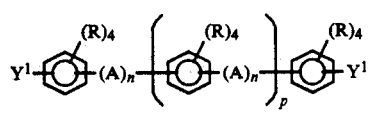

Formula VI

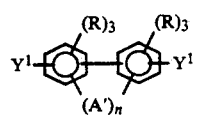

Formula VII

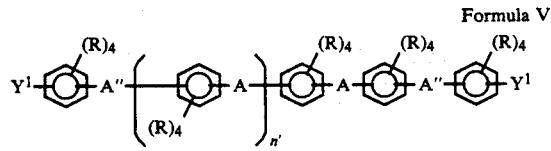

Formula VIII wherein at least about 80 percent of the —A— linkages in Formulas V, VI and VIII and the direct bond between the two aromatic rings in Formula VII and the $Y^1$ groups are in the para position with respect to each other; one $Y^1$ group is —OH and the other is —$NH_2$; each A, A', A", $A^1$, R, $R^1$, n, n' and p are as hereinbefore defined. The aromatic rings can also contain one or more heteroatoms selected from N, O, S and the like.

The term hydrocarbyl as employed herein means any aliphatic, cycloaliphatic, aromatic, aryl substituted aliphatic or cycloaliphatic, or aliphatic or cycloaliphatic substituted aromatic group. The aliphatic or cycloaliphatic groups can be saturated or unsaturated. When applied to the A' group of Formulas III and VII, the hydrocarbyl group can also contain one or more heteroatoms selected from N, O, S and the like. Likewise, the term hydrocarbyloxy means a hydrocarbyl group having an oxygen linkage between it and the carbon atom to which it is attached.

Particularly suitable aminophenols are, for example,

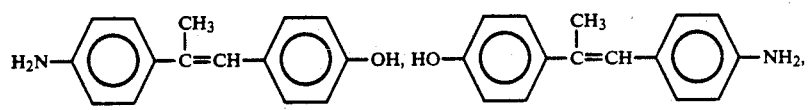

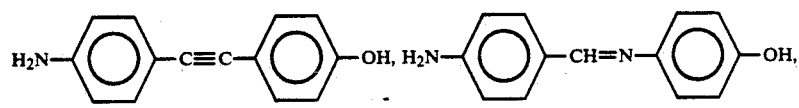

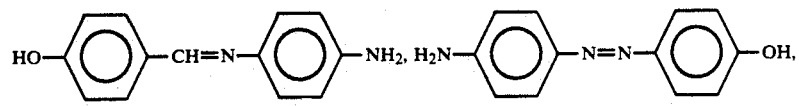

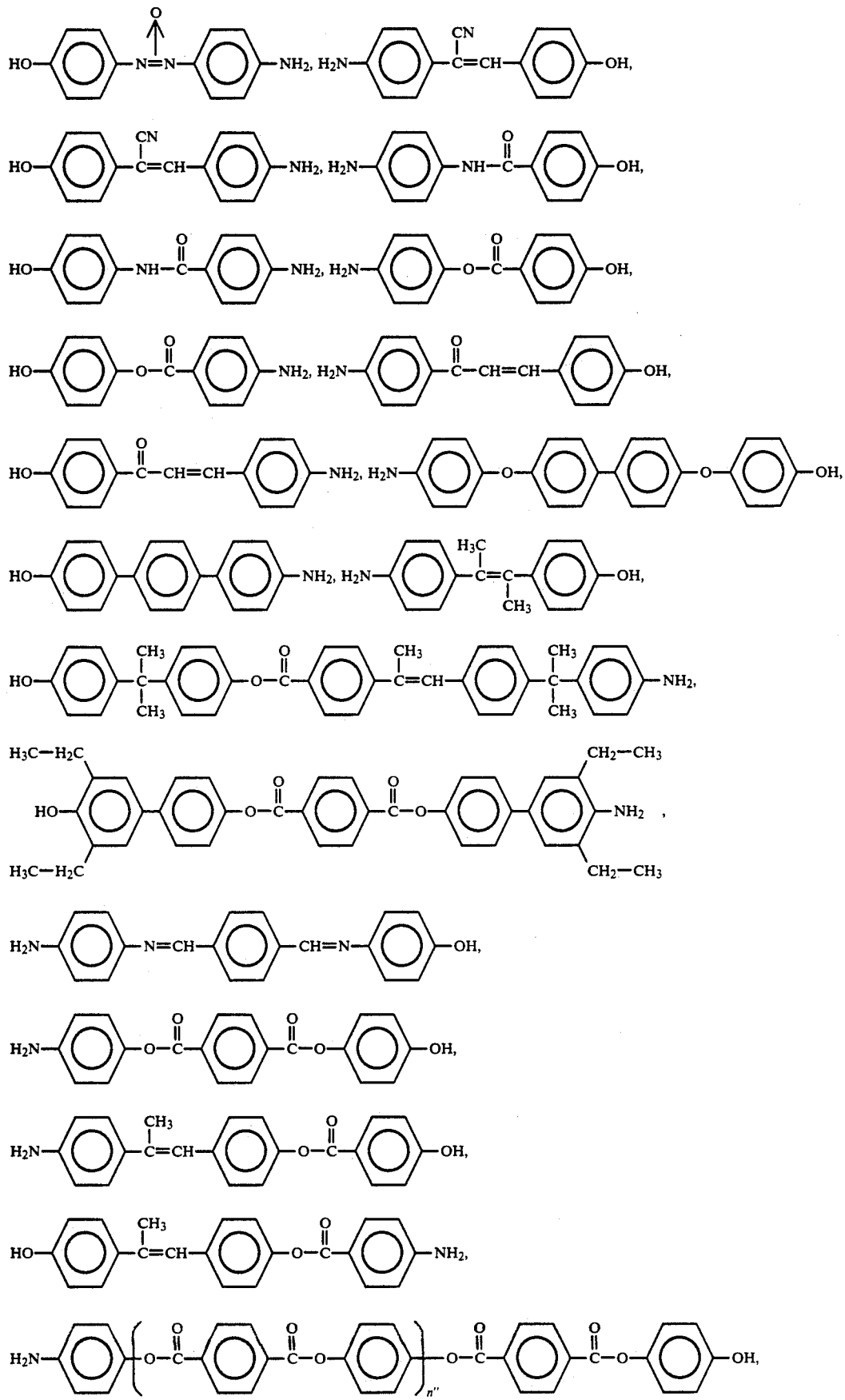

-continued
wherein n" has a value from 1 to about 10,
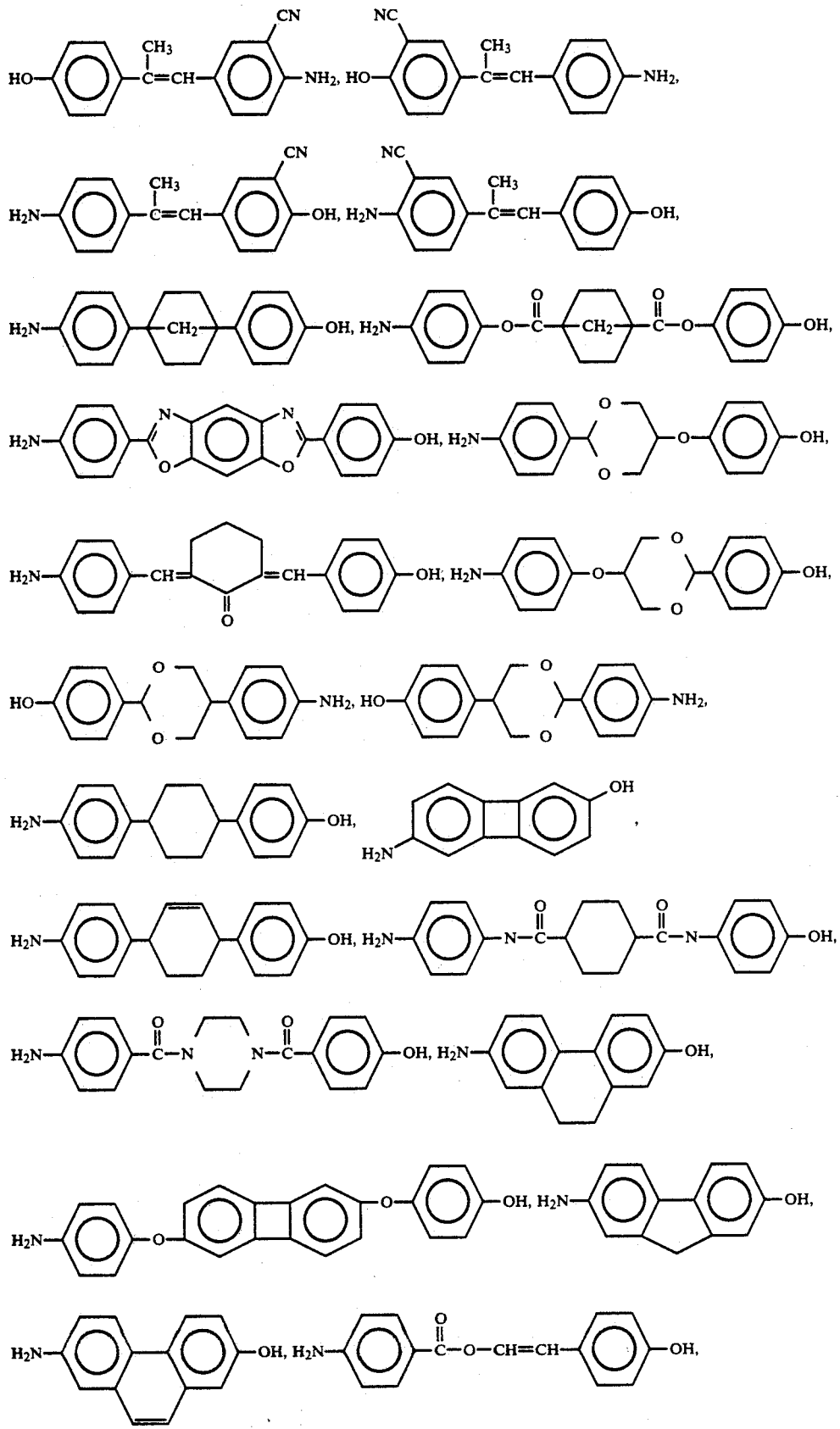

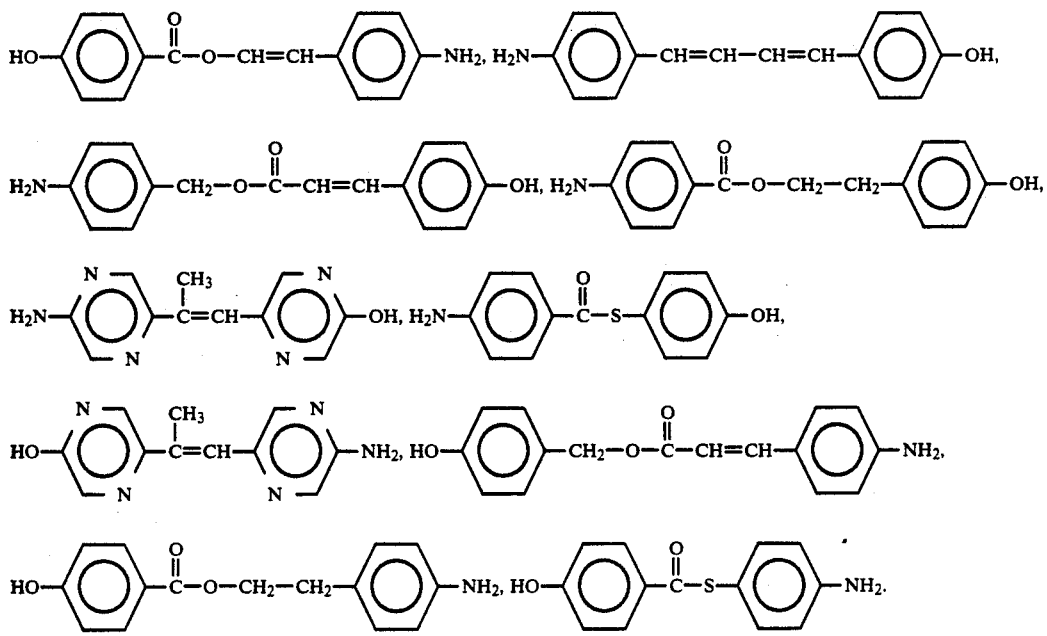

mixtures thereof and the like.

Suitable maleic anhydrides include, for example, those represented by the Formula IX

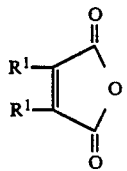

Formula IX wherein $R^1$ is as hereinbefore defined. Suitable maleic anhydrides include maleic anhydride, methyl maleic anhydride, mixtures thereof and the like. Most preferred as the maleic anhydride is maleic anhydride per se.

Suitable solvents include aliphatic monocarboxylic acids such as acetic acid, propionic acid, mixtures thereof and the like. Most preferred as the solvent is acetic acid. The maleamic acid resulting from reaction of a maleic anhydride and an amionphenol compound, typically in an inert solvent such as chloroform, toluene or dioxane, may be isolated then dehydrated in an aliphatic monocarboxylic acid to the corresponding phenolic functional maleimide. Alternately, the reaction may be performed in a single continuous step in the aliphatic monocarboxylic acid solvent. The product resulting from this reaction is a phenolic functional maleimide represented by the Formulas X, XI, XII and XIII

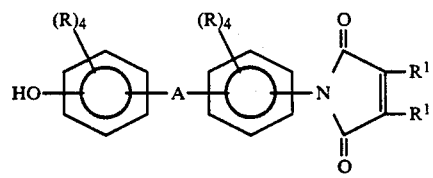

Formula X

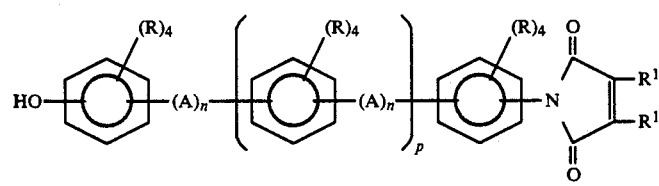

Formula XI

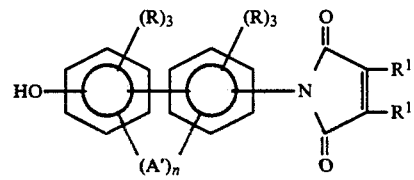

Formula XII

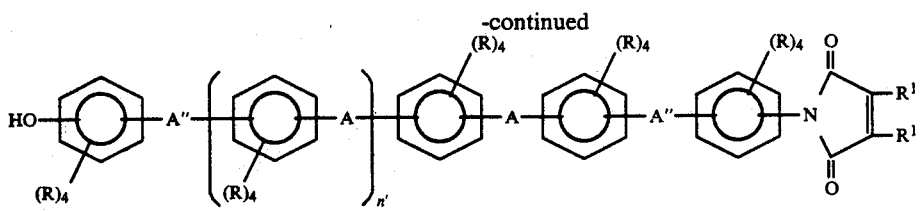

Formula XIII wherein R, R¹, A, A', A", A¹, n, n' and p are as hereinbefore defined.

Cyanate functional maleimide compositions containing one or more rodlike mesogenic moieties are conveniently prepared by reacting a stoichiometric quantity up to a slight stoichiometric excess (up to about 20 percent excess) of a cyanogen halide with a phenolic functional maleimide containing one or more rodlike mesogenic moieties, such as those represented by Formulas X, XI, XII and XIII, in the presence of a stoichiometric quantity of a base material.

Suitable cyanogen halides include cyanogen chloride and cyanogen bromide. Alternately, the method of Martin and Bauer described in *Organic Synthesis*, volume 61, pages 35–68 (1983) published by John Wiley and Sons, which is incorporated herein by reference, can be used to generate the required cyanogen halide in situ from sodium cyanide and a halogen such as chlorine or bromine.

Suitable base compounds include both inorganic bases and tertiary amines such as sodium hydroxide, potassium hydroxide, trimethylamine, triethylamine, mixtures thereof, and the like. Triethylamine is most preferred as the base.

Suitable solvents for the cyanation reaction include water, aliphatic ketones, chlorinated hydrocarbons, aliphatic and cycloaliphatic ethers and diethers, aromatic hydrocarbons, mixtures thereof and the like. Acetone, methylethylketone, methylene chloride or chloroform are particularly suitable as the solvent. Reaction temperatures of from about $-40°$ C. to about $60°$ C. are operable, with reaction temperatures of $-15°$ C. to $10°$ C. being preferred. Reaction times can vary substantially, for example, as a function of the reactants being employed, the reaction temperature, solvent(s) used, the scale of the reaction, and the like, but are generally between 15 minutes and 4 hours. with reaction times of 30 minutes to 90 minutes being preferred.

Curing of the Cyanate Functional Maleimides Containing One or More Rodlike Mesogenic Moieties The cyanate functional maleimides containing one or more rodlike mesogenic structure(s) are cured (thermoset) by heating from about $50°$ C. to about $400°$ C., preferably by heating from $100°$ C. to $250°$ C., optionally in the presence of a suitable catalyst. Suitable catalysts include, for example, acids, bases, salts, free radical forming materials, nitrogen and phosphorus compounds, such as for example, Lewis acids such as $AlCl_3$, $BF_3$, $FeCl_3$, $TiCl_4$, $ZnCl_2$, $SnCl_4$; protonic acids such as HCl, $H_3PO_4$; aromatic hydroxy compounds such as phenol, p-nitrophenol, pyrocatechol, dihydroxynaphthalene; organic peroxides and hydroperoxides such as t-butylperoxybenzoate, benzoyl peroxide, t-butylhydroperoxide; azo and diazo compounds such as azobisisobutyronitrile; sodium hydroxide, sodium methylate, sodium phenolate, trimethylamine. triethylamine, tributylamine, diazabicyclo-[2.2.2]-octane, quinoline, isoquinoline, tetrahydroisoquinoline, tetraethylammonium chloride, pyridine-N-oxide, tributyl phosphine, zinc octoate, tin octoate, zinc naphthenate, cobalt naphthenate, cobalt octoate, cobalt acetylacetonate and the like. Also suitable as catalysts are the metal chelates such as, for example, the chelates of transition metals and bidentate or tridentate ligands, particularly the chelates of iron, cobalt, zinc, copper, manganese, zirconium, titanium, vanadium, aluminum and magnesium. These and other operable catalysts are disclosed in U.S. Pat. Nos. 3,694,410 and 4,094,852 which are incorporated herein by reference in their entirety. Cobalt naphthenate, cobalt octoate and cobalt acetylacetonate are most preferred as the catalysts. The quantity of catalyst used, if any, depends on the structure of the particular catalyst, the structure of the cyanate functional maleimide being cured, the cure temperature, the cure time, and the like. Generally, catalyst concentrations of from about 0.001 to about 2 percent by weight are preferred.

B-staging or prepolymerization of the compositions of the cyanate functional maleimides of the present invention can be accomplished by using lower temperatures and/or shorter curing times. Curing of the thus formed B-staged (prepolymerized) resin can then be accomplished at a later time or immediately following B-staging (prepolymerization) by increasing the temperature and/or curing time.

The cured (thermoset) products prepared from the cyanate functional maleimides containing rodlike mesogenic structure(s) possess a complex variety of curing structures including the cyanate group homopolymerization structure

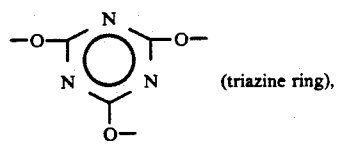

(triazine ring), the maleimide group homopolymerization structure

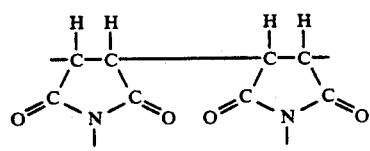

and cyanate group and maleimide group copolymerization structures such as, for example,

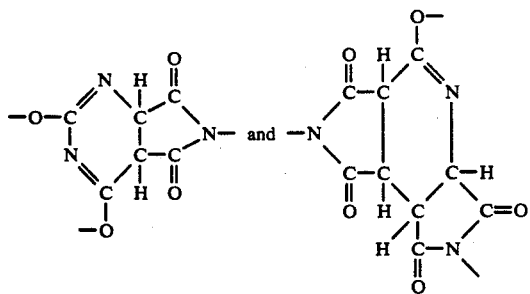

unless other functionalities are present in the polycyanate that participate in the curing process.

Polycyanates or Polycyanamides which do not Contain Rodlike esogenic Moieties and which can be Employed in the Curable and Cured Compositions Suitable polycyanates or polycyanamides which do not contain rodlike mesogenic structures and which can be employed to prepare the polymerizable mixtures of the present invention include, for example, those represented by the following Formulas XIV, XV, XVI and XVII

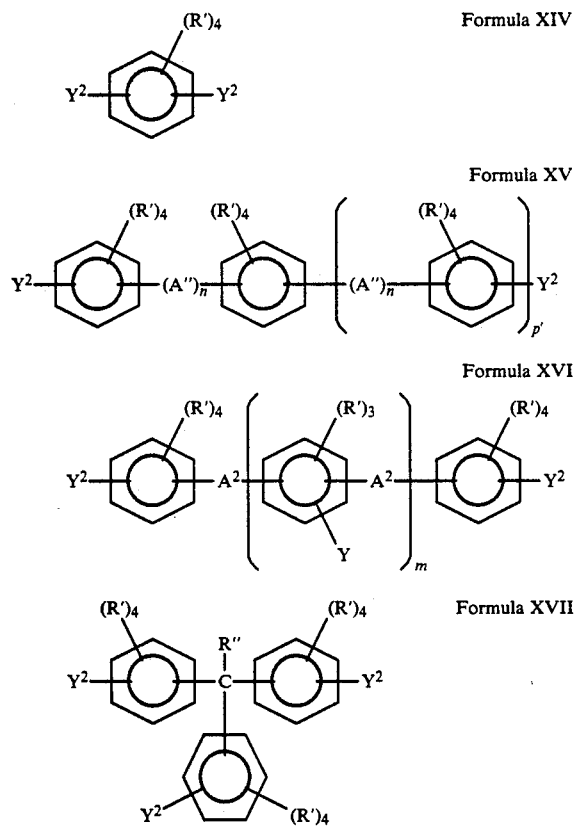

wherein A" and n are as hereinbefore defined; each $Y^2$ is a —O—C≡N or a —NR$^1$—C≡N group; each $A^2$ is independently an alkylene group having from 1 to about 10, preferably from 1 to about 4 carbon atoms or a

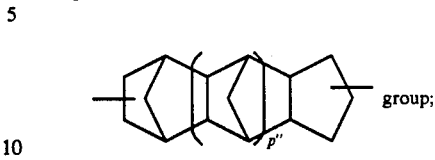

group;

each R' is independently hydrogen, a hydrocarbyl or hydrocarbyloxy group having from 1 to about 10, preferably 1 to about 4 carbon atoms, a halogen, preferably chlorine or bromine, a phenyl group, a —O—C≡N group, or a —NR$^1$—C≡N group; each R" is independently hydrogen, a hydrocarbyl or hydrocarbyloxy group having from 1 to about 10, preferably 1 to about 4 carbon atoms, a halogen, preferably chlorine or bromine, or a phenyl group; p' has a value from zero to about 100, preferably from zero to about 30; p" has a value of from zero to about 10, preferably from zero to 3 and m has a value of from about 0.001 to about 6, preferably from about 0.01 to about 3. The aromatic rings can also contain one or more heteroatoms selected from N, O, S and the like.

Suitable polycyanates or polycyanamides which do not contain rodlike mesogenic structures represented by Formulas XIV, XV, XVI and XVII include, for example, bisphenol A dicyanate, the dicyanates of 4,4'-dihydroxydiphenyl oxide, resorcinol, hydroquinone, 4,4'-thiodiphenol, 4,4'-sulfonyldiphenol, 3,3',5,5'-tetrabromobisphenol A, 2,2',6,6'-tetrabromobisphenol A, 2,2'-dihydroxydiphenyl, 3,3'-dimethoxybisphenol A, 4,4'-dihydroxydiphenylcarbonate, dicyclopentadiene diphenol, 4,4'-dihydroxybenzophenone, 4,4'-dihydroxydiphenyl methane, tricyclopentadiene diphenol, the tricyanate of tris(hydroxyphenyl)methane, the tetracyanate of 2,2',4,4'-tetrahydroxydiphenyl methane, the polycyanate of a phenolformaldehyde condensation product (novolac), the polycyanate of a dicyclopentadiene and phenol condensation product, the dicyanamide of 4,4'-diaminodiphenyl methane, the cyanate cyanamide of p-aminophenol, and the like.

The polycyanates or polycyanamides which do not contain rodlike mesogenic structures are prepared using the corresponding polyphenol, polyamine or aminophenol precursor and the previously described cyanation (cyanamidation) chemistry.

Epoxy Resins which can be Employed in the Curable and Cured Compositions

Suitable epoxy resins which can be employed to prepare the polymerizable mixtures of the present invention include materials having an average of more than one vicinal epoxide group per molecule, such as, for example, the epoxy resins represented by the following Formulas XVIII, XIX, XX, XXI, XXII, XXIII, XXIV, XXV, XXVI, XXVII Formula XVIII

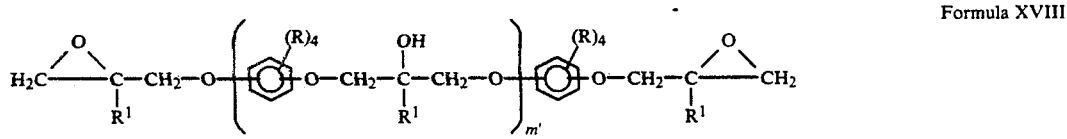

Formula XIX
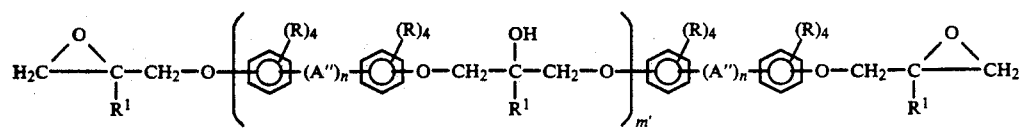
Formula XX
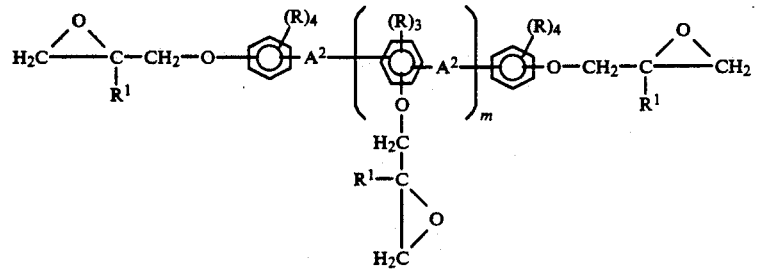
Formula XXI
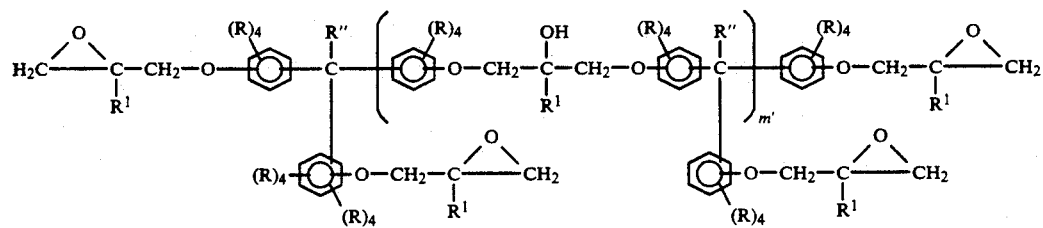
Formula XXII
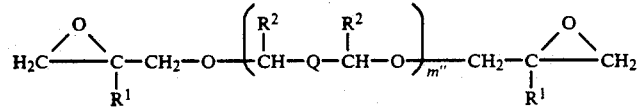
Formula XXIII
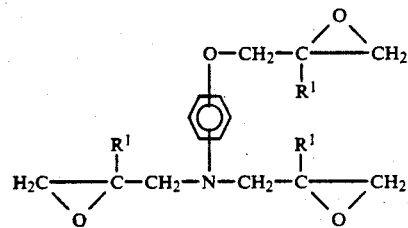
Formula XXIV
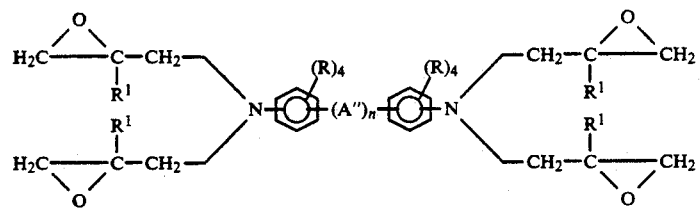
Formula XXV
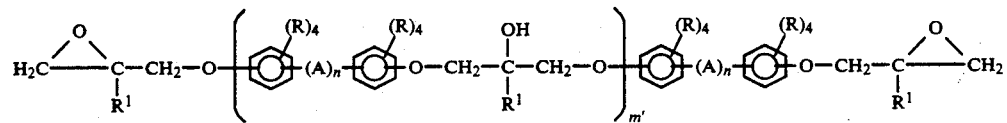
Formula XXVI
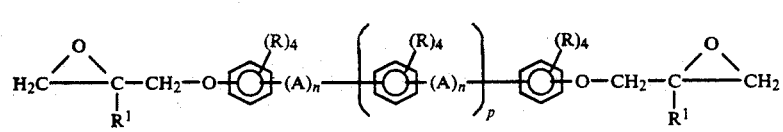

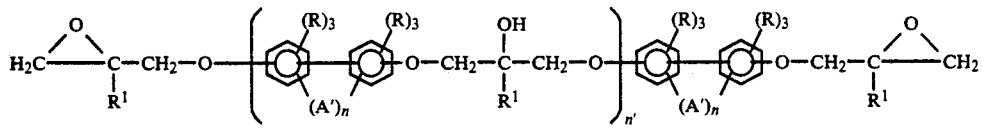

Formula XXVII wherein A, $A^2$, A', A", R, R, R", m and n are as hereinbefore defined; each $R^2$ is independently hydrogen, or a hydrocarbyl or halohydrocarbyl group having from 1 to about 6, preferably 1 to about 2 carbon atoms; Q is a direct bond, —$CH_2$—S—$CH_2$—, —$(CH_2)_{n'''}$—, or

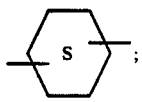

m' has a value of from zero to about 30, preferably from about zero to about 5; m" has a value from 1 to about 10, preferably from about 1 to about 4 and n" has an average value from about 1 to about 10. The aromatic rings can also contain one or more heteroatoms selected from N, O, S and the like.

Particularly suitable epoxy resins represented by Formulas XXVIII, XIX, XX, XXI, XXII, XXIII, XXIV, XXV, XXVI and XXVII are the diglycidyl ethers of resorcinol, hydroquinone, dihydroxydiphenyl methane, bisphenol A, 3,3',5,5'-tetrabromobisphenol A, 4,4'-sulfonyldiphenol, 4,4'-thiodiphenol, 4,4'-dihydroxydiphenyl oxide, 4,4'-dihydroxybenzophenone, 2,2'-dihydroxydiphenyl, dicyclopentadiene diphenol, tricyclopentadiene diphenol, 4,4'-dihydroxydiphenyl, 4,4'-dihydroxystilbene, 4,4'-dihydroxy-alpha-methylstilbene, 4,4'-dihydroxy-alpha-cyanostilbene, 4,4'-dihydroxychalcone, 4,4'-dihydroxydiphenylacetylene, 4,4'-dihydroxydiphenylazomeshine, 4,4'-hydroxyazobenzene, 4,4'-bis(4-hydroxyphenoxy)diphenyl, 4,4'-dihydroxybenzanilide, ethylene glycol, thiodiglycol, diethylene glycol, dipropylene glycol, polypropylene glycol, polyethylene glycol, 1,4-cyclohexanediol, dibutylene glycol, the advancement reaction product of the diglycidyl ether of bisphenol A and bisphenol A, the advancement reaction product of the diglycidyl ether of 4,4'-dihydroxy-alpha-methylstilbene and 4,4'-dihydroxy-alpha-methylstilbene, the triepoxide of p-aminophenol, the tetraepoxide of 4,4'-diaminodiphenyl methane, the triglycidyl ether of tris(hydroxyphenyl)methane, the tetraglycidyl ether of 2,2',4,4'-tetrahydroxydiphenyl methane, the polyglycidyl ether of a phenolformaldehyde condensation product (novolac), the polyglycidyl ether of a dicyclopentadiene or oligomer thereof and phenol or halogen or alkyl substituted phenol condensation product and the like.

The aforementioned epoxy resins can be prepared by reaction of a polyphenol (polyamine, aminophenol, polyalkylene glycol) with an epihalohydrin and a basic acting material. Said reaction generally involves two distinct steps: coupling reaction of the epihalohydrin and polyphenol to provide a halohydrin intermediate and dehydrohalogenation reaction of the halohydrin intermediate to provide the glycidyl ether product. Suitable catalysys and reaction conditions for preparing epoxy resins are described in the *Handbook of Epoxy Resins* by Lee and Neville, McGraw-Hill (1967) which is incorporated herein by reference.

Polymaleimides for Use in the Curable and Cured Compositions

Suitable polymaleimides which can be employed to prepare the polymerizable mixtures of the present invention include, for example, those represented by the Formulas XXVIII, XXIX, XXX, XXXI, XXXII, XXXIII, XXXIV and XXXV

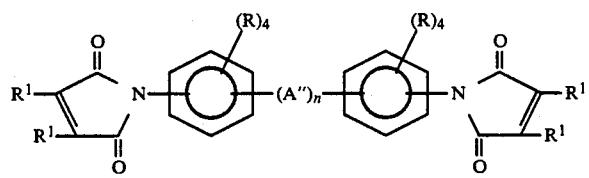

Formula XXVIII

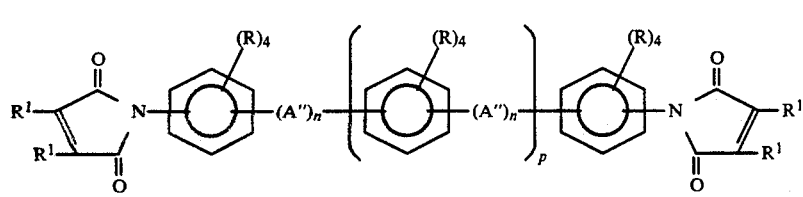

Formula XXIX

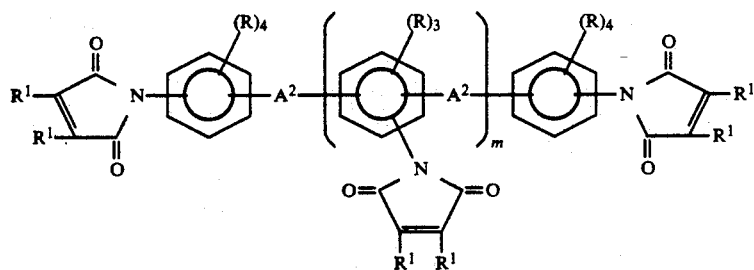

Formula XXX

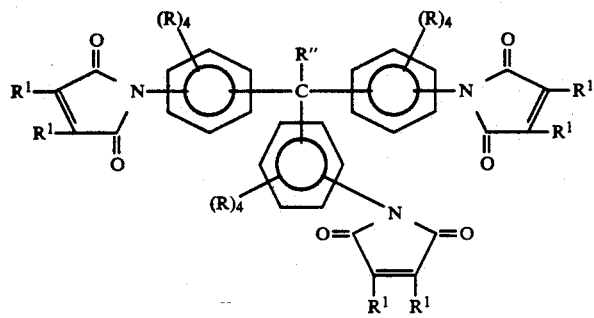

Formula XXXI

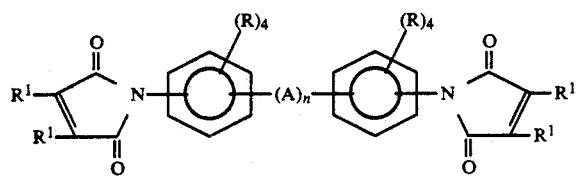

Formula XXXII

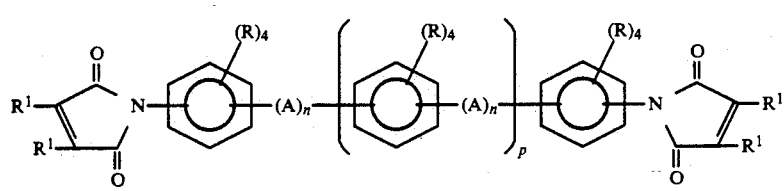

Formula XXXIII

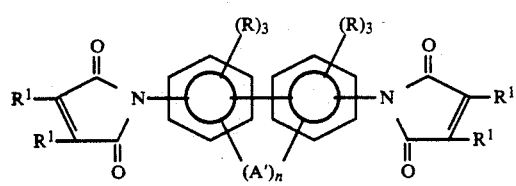

Formula XXXIV

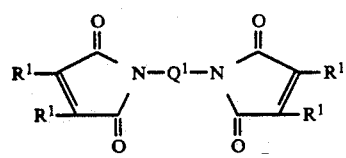

Formula XXXV wherein A, $A^2$, A', A'', R, $R^1$, R'', m, n and p are as hereinbefore defined and Q' is a divalent hydrocarbyl group having from 2 to about 12 carbon atoms and may be linear or branched aliphatic, cycloaliphatic or polycycloaliphatic. The aromatic rings can also contain one or more heteroatoms selected from N, O, S and the like.

Particularly suitable polymaleimides represented by Formulas XXVIII, XXIX, XXX. XXXI, XXXII, XXXIII, XXXIV and XXXV are N,N'-ethylenebismaleimide, N,N'-ethylenebis(2-methylmaleimide), N,N'-hexamethylenebismaleimide, N,N'-(oxydi-p-phenylene)bismaleimide, N,N'-(methylenedi-p-phenylene)maleimide, N,N'-(methylenedi-p-phenylene)bis(2-methylmaleimide), N,N'-(thio-di-p-phenylene)bismaleimide, N,N'-(sulfonyldi-m-phenylene)bismaleimide, N,N'-(isopropylidenedi-p-phenylene)bismaleimide, polymethylene polyphenylene polymaleimides, the bismaleimide of 4,4'-diaminostilbene, the bismaleimide of 4,4'-diaminobenzanilide and the like.

The polymaleimides can be prepared by reacting a stoichiometric quantity of a maleic anhydride per amine group with a polyamine in the presence of a suitable solvent, such as, for example, aromatic hydrocarbons, chlorinated hydrocarbons or N,N-dimethylformamide. The polymaleamic acid resulting from reaction of a maleic anhydride and a polyamine may be isolated and dehydrated to the desired polymaleimide. Alternately, the reaction may be performed in a single continuous step. Detailed procedures for preparing polymaleimide3 can be found in U.S. Pat. Nos. 2,444,536; 2,462,835; and *Journal of Polymer Science: Part A: Polymer Chemistry*, Vol. 27, pages 375-388 (1989) which are incorporated herein by reference.

Polyamines Suitable for Use in the Curable and Cured Compositions

Suitable polyamines which can be employed to prepare the polymerizable mixtures of the present invention, include those containing one or more of the rodlike mesogenic structure(s) already described herein, as well as any of the other known polyamines which do not contain rodlike mesogenic structures. Typical representatives of said polyamines free of rodlike mesogenic structures include 1,4-diaminobutane, 1,6-hexanediamine, 1,12-diaminododecane, 2-methyl-4-ethyl-1,8-diaminooetane, 1,4-diamino-cyclohexane, 4,4'-diaminodiphenyl methane, 1,4-diaminobenzene, tris-(aminophenyl)methane, anilineformaldehyde condensation products and the like.

Polyphenols Suitable for Use in the Curable and Cured Compositions

Suitable polyphenols which can be employed to prepare the polymerizable mixtures of the present invention, include those containing one or more of the rodlike mesogenic structure(s) already described herein as well as any of the other known polyphenols which do not contain rodlike mesogenic structures. Typical representatives of said polyphenols free of rodlike mesogenic structures include resorcinol, 4,4'-sulfonyldiphenol, 4,4'-dihydroxydiphenyl oxide, tris(hydroxyphenyl)methane, phenolformaldehyde condensation products and the like.

Polymerizable Unsaturated Monomers Suitable for Use in the Curable and Cured Compositions Suitable compounds containing one or more polymerizable ethylenically unsaturated group(s) which can be employed to prepare the polymerizable mixtures of the present invention include both those containing one or more rodlike mesogenic structure(s) and those free of said structures.

Suitable polymerizable ethylenically unsaturated monomers containing one or more rodlike mesogenic moieties are cataloged by Alexandre Blumstein in *Liquid Crystalline Order in Polymers*, published by Academic Press, New York (1978) on pages 105-140; *Mesomorphic Order in Polymers and Polymerization in Liquid Crystalline Media* published by American Chemical Society (ACS Symposium Series 74), Washington, D.C. (1978) on pages 56-70; and N. A. Plate and V. P. Shibaev in *Comb-Shaped Polymers and Liquid Crystals* published by Plenum Press, New York (1987) on pages 1-415; V. Percec, et. al., *Polymer Bulletin*, 17, pages 347-352 (1987); R. Duran and P. Gramain, *Makromol. Chem.*, 188, pages 2001-2009 (1987); A. M. Mousa, et. al., *Polymer Bulletin*, 6, pages 485-492 (1982); H. Finkelmann, et. al., *Makromol. Chem.*, 179, pages 829-832 (1978); M. Portugall, et. al., *Makromol. Chem.*, 183, pages 2311-2321 (1982) and U.S. Pat. Nos. 4,637,896 and 4,614,619, all of which are incorporated herein by reference. Suitable polymerizable ethylenically unsaturated monomers containing one or more rodlike mesogenic moieties per molecule are represented by the Formulas XXXVI or XXXVII:

$$M-Q^2 \quad \text{FORMULA XXXVI}$$

$$M-(Q^3)_n-R^3-Q^2 \quad \text{FORMULA XXXVII}$$

wherein n and $R^1$ are as hereinbefore defined, M is a group containing two or more aromatic rings bridged by a rigid central linkage, $R^3$ is a divalent hydrocarbon group having from one to about 12 carbon atoms and may be linear, branched, cyclic, aromatic or a combination thereof and may be substituted with one or more inert groups, such as, for example, a methoxy group, or may contain one or more inert heteroatom containing linkages, such as, for example, an ether linkage; $Q^3$ is $-O-$, $-NR^1-$, $-S-$, $-O-CO-$, $-CO-O-$, $-NR^1-CO-$, $-CO-NR^1-$, $-CO-$, $-O-CO-O-$, $-S-CO-$, $-CO-S-$, $-NR^1-CO-O-$, $-O-CO-NR^1-$, $-NR^1-CO-NR^1-$; and $Q^2$ is a polymerizable ethylenically unsaturated group. As a class, these monomers generally contain a $-CH=CH_2$, allyl, methallyl, propenyl, isopropenyl, acrylate or methacrylate group as the polymerizable ethylenically unsaturated group and a linear divalent aliphatic, aliphatic ether, aliphatic polyether, aliphatic thioether or cycloaliphatic flexible spacer connecting the polymerizable ethylenically unsaturated group and the rodlike mesogenic group(s) through a heteroatom linkage. Typical rodlike mesogenic groups include those wherein two or more aromatic rings are bridged by a rigid central linkage wherein said rigid central linkage is required to bridge the aromatic rings to provide at least about 80 percent para substitution. The aromatic rings can be inertly substituted, however, unsubstituted aromatic rings which maximize the molecular aspect ratio are preferred. Also preferred is a single inert substituent in the para position on the ring not connected to the polymerizable ethylenically unsaturated group (either directly or via a flexible spacer). This type of substituent can be used to enhance the molecular aspect ratio. Typical of these inert substituents are $CH_3O-$, $Cl-$, $NO_2-$, $-C\equiv N$ and the like. The aromatic rings can also contain one or more heteroatoms selected from N, O, S and the like. Typical rigid central linkage groups for bridging the aromatic rings include, for example, a direct bond, $-CR^1=CR^1-$, $-C\equiv-C-$, $-N=N-$, $-CR^1=N-$, $-CR^1=N-N=CR^1-$, $-CR^1=C-R^1-CO-$, $-O-CO-$, $-NR^1-CO-$, $-CO-O-$, $-CO-NR^1-$, $-CO-CR^1=CR^1-$, $-CR^1=C-R^1-O-CO-(CH_2)_{n'}-$, $-N=CR^1-$, $-(CH_2)-{n'}-CO-O-CR^1=CR^1-$, $-CR^1=CR^1-O-CO-$, $-CO-O-CR^1=CR^1-$, $-CO-O-N=CR^1-$, $-CR^1=N-O-CO-$, $-CR^1=CR^1-CO-O-$, $-CO-S-$, $-O-CO-CR^1=CR^1-$, $-CR^1=C-R^1-CO-O-(CH_2)_{n'}-$, $-S-CO-$, $-(CH_2)-{n'}-O-CO-CR^1=CR^1-$, $-CHR^1-CH-R^1-CO-O-$, $-O-CO-CHR^1-CHR^1-$, $-C\equiv-C-C\equiv-C-$, $-CR^1=CR^1-CR^1=CR^1-$, $-CO-NR^1-NR^1-CO-$,

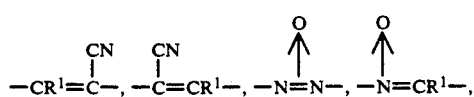

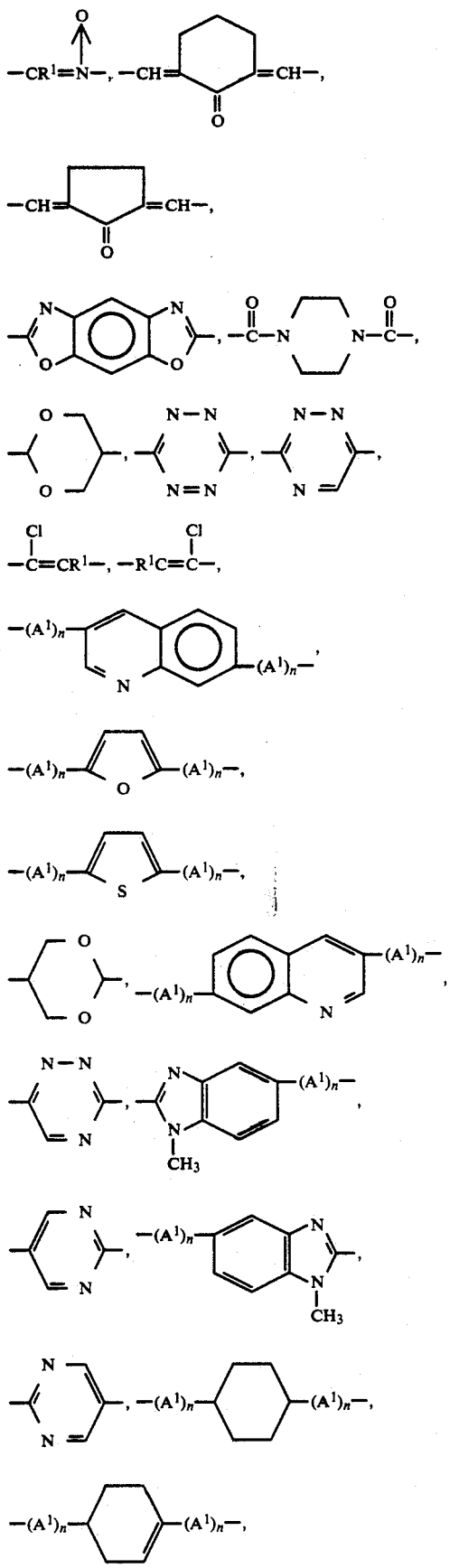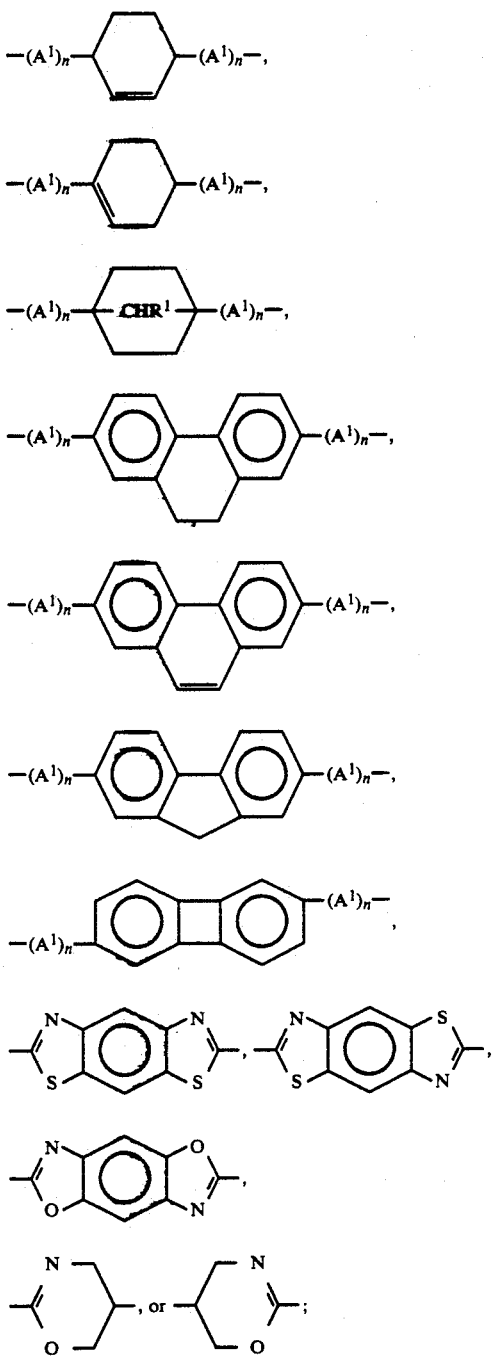

and the like; wherein $R^1$, $A^1$, n and n' are as hereinbefore defined. As is well known in the prior art, all or a part of the aromatic rings can be replaced with other promesogenic structures, such as, for example, the trans-cyclohexane ring or a cholesterol group. Additionally, it is has been demonstrated in the prior art that efficacious rodlike mesogen containing polymerizable ethylenically unsaturated monomers can be prepared with omission of the flexible spacer between the polymerizable ethylenically unsaturated group and the rodlike mesogenic group(s).

Generally, the ethylenically unsaturated monomers containing $-CH=CH_2$, acrylate, allyl, methallyl, propenyl, isopropenyl or methacrylate as the polymerizable vinyl group and a linear divalent hydrocarbon group connecting the vinyl group and the rodlike mesogenic group through heteroatom containing functional groups between the hydrocarbon spacer and the mesogenic group are most preferred. Thus, a mesogenic group ether linked to a —CH$_2$—CH$_2$— which is in turn linked to provide a methacrylate ester, that is,

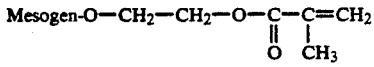

or a mesogenic group linked to a vinyl group, that is,

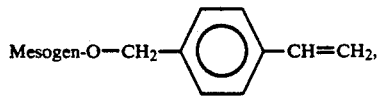

are examples of those species preferred as the ethylenically unsaturated monomer containing one or more rodlike mesogenic moieties.

Particularly suitable ethylenically unsaturated monomers containing a rodlike mesogenic moiety include, for example,

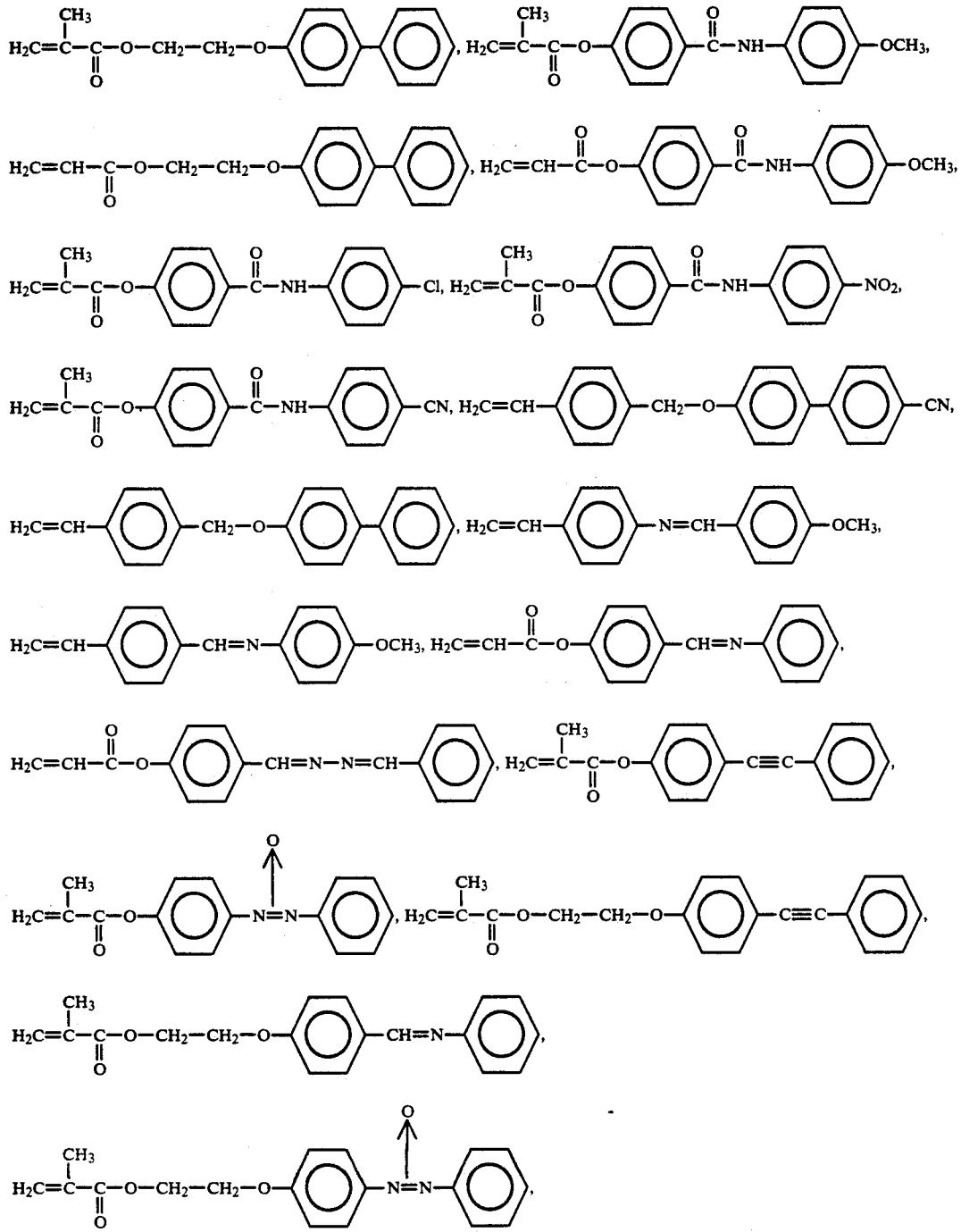

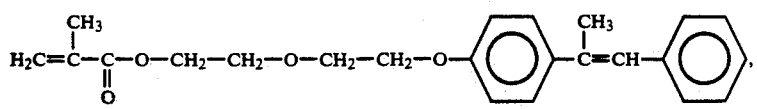
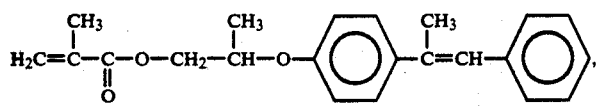
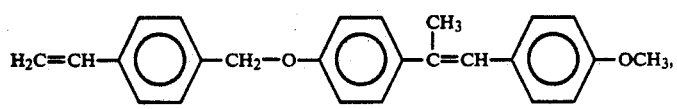
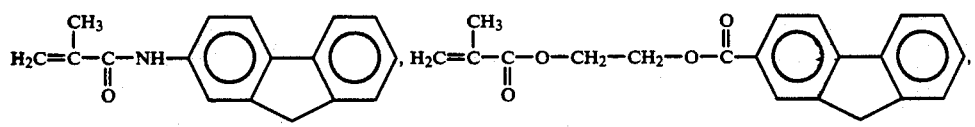
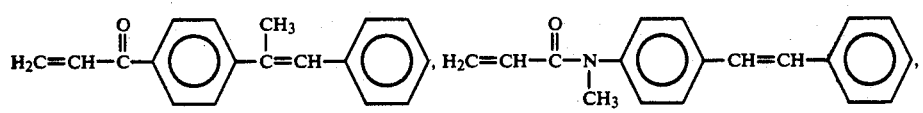
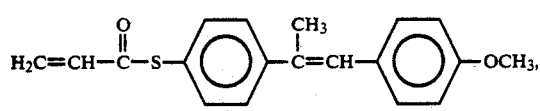
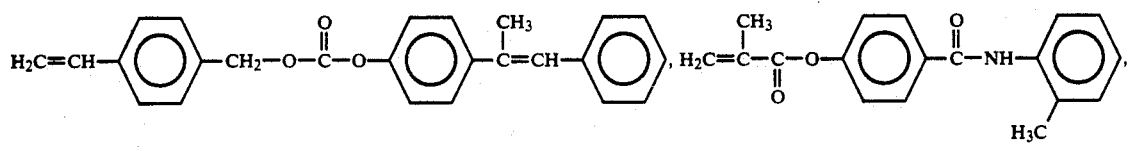
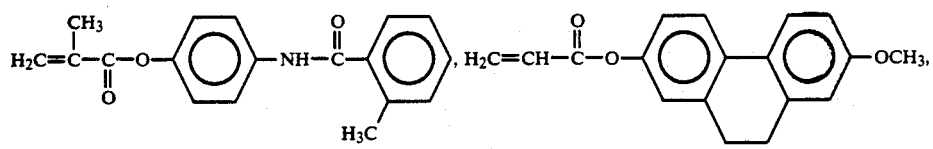
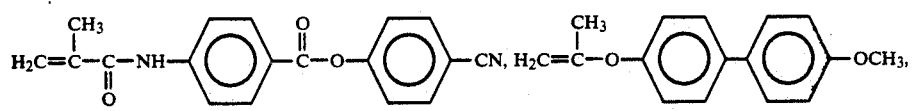
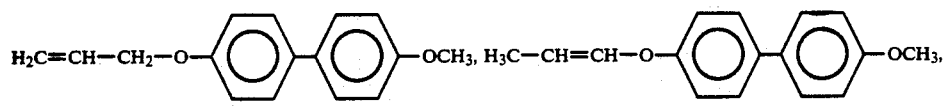
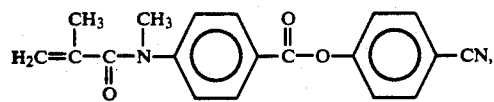
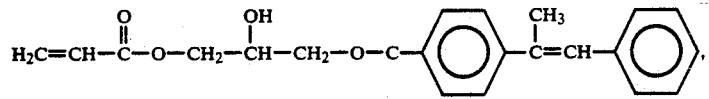
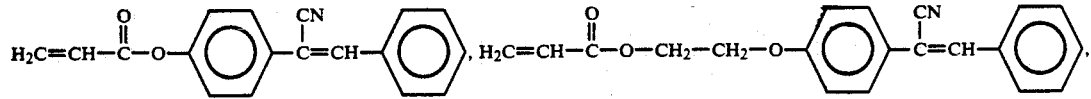

-continued

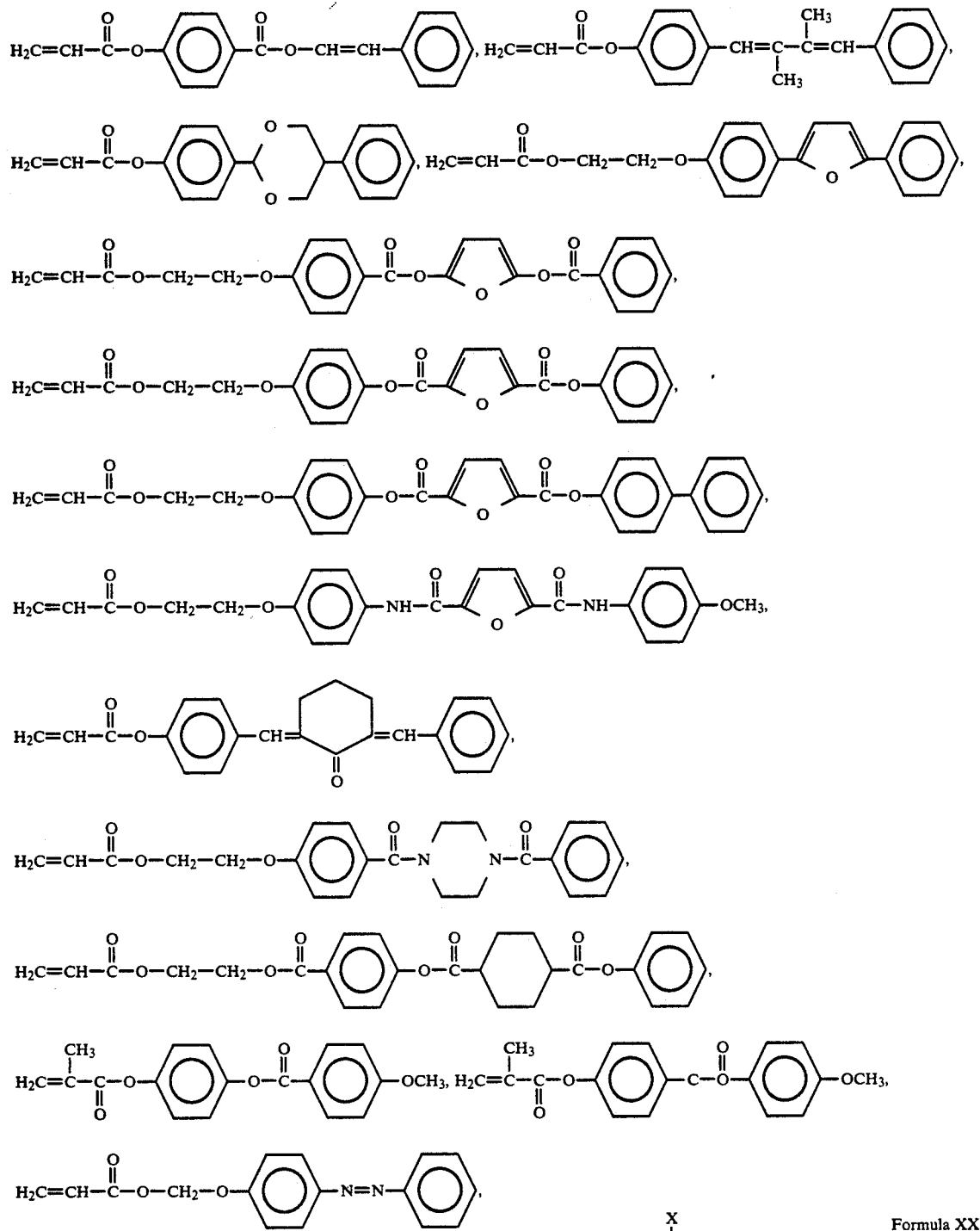

any combination thereof and the like.

Suitable polymerizable ethylenically unsaturated monomers which do not contain rodlike mesogenic structures can be selected from the many known classes of polymerizable vinyl monomers. Suitable such monomers include, for example, the vinyl aromatic compounds represented by the following Formula XXXVIII

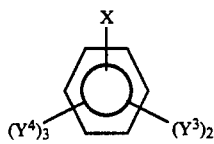

Formula XXXVIII wherein each $R^1$ is as hereinbefore defined, $Y^3$ is independently hydrogen, a hydrocarbyl or hydrocarbyloxy group having from 1 to about 5 carbon atoms, a vinyl group, an allyl group, a methallyl group, a propenyl group, a isopropenyl group, a nitro group, a nitrile group, a halogen, such as chlorine or bromine or fluorine, or a —CO—R$^1$ group; each Y$^4$ is independently hydrogen, a hydrocarbyl or hydrocarbyloxy group having from 1 to about 5 carbon atoms, or a halogen, such as chlorine or bromine or fluorine and X is

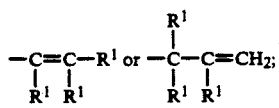

or the acrylate or methacrylate compounds represented by the following Formula XXXIX

Formula XXXIX wherein R$^4$ is a hydrocarbyl group having from 2 to about 25 carbon atoms and may be branched, cyclic, polycyclic, saturated or unsaturated and R$^5$ is hydrogen or a methyl group.

Typical polymerizable unsaturated monomers represented by Formula XXXVIII include, for example, styrene, alpha-methylstyrene, o-, m-, p-chlorostyrene; o-, m-, p-bromostyrene; o-, m-, p-tert-butylstyrene; o-, m-, p-methylstyrene; o-, m-, p-methoxystyrene; divinylbenzenes, trivinylbenzenes, o-, M-, p-isopropenylstyrene; o-, m-, p-allylstyrene; o-, m-, p-methallylstyrene; allylbenzene, methallylbenzene, diallylbenzenes and the like.

Typical acrylate (methacrylate) esters represented by Formula XXXIX include, for example, ethyl acrylate, n-butyl acrylate, n-butyl methacrylate, secbutyl acrylate, 2-ethylhexyl acrylate, 2-ethylhexyl methacrylate, n-dodecyl acrylate, cyclohexyl acrylate, methylcyclohexyl acrylate, norbornyl acrylate, dicyclopentadiene acrylate, methyldicyclopentadiene acrylate and the like.

Other suitable monomers include the acidic monomers, such as acrylic and methacrylic acid; the amide monomers, such as acrylamide and N-methylacrylamide; the allyl monomers, such as diallylphthalate, triallylisocyanurate, diallylmaleate and dimethallylfumarate; the vinyl halides, such as vinyl chloride and vinyl bromide; the vinyl esters, such as vinyl acetate; the vinyl di and polycyclic aromatics, such as vinyl naphthalene; the vinyl nitriles, such as acrylonitrile; and the hydroxyalkyl acrylates and methacrylates, such as 2-hydroxyethyl acrylate.

Compounds Containing Both a Cyanate or Cyanamide Group and a Polymerizable Ethylenically Unsaturated Group for Use in the Curable and Cured Compositions Suitable compounds which contain both a cyanate or cyanamide group and a polymerizable ethylenically unsaturated group in the same molecule that can be used to prepare the polymerizable mixtures of the present invention include, for example, those represented by the following Formula XXXX

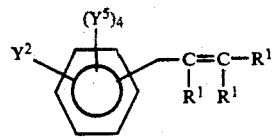

Formula XXXX wherein each Y$^2$ and R$^1$ are as hereinbefore defined, Y$^5$ is independently hydrogen, a hydrocarbyl or hydrocarbyloxy group having from 1 to about 12 carbon atoms, a nitro group, a nitrile group, a halogen, such as chlorine or bromine or fluorine, or a —CO—R$^1$ group; or a compound represented by the following Formula XXXXI

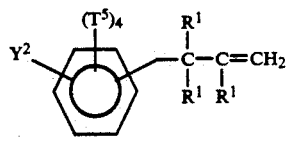

Formula XXXXI wherein each Y$^2$, Y$^5$ and R$^1$ are as hereinbefore defined.

Suitable compounds which contain a cyanate or cyanamide group and a polymerizable ethylenically unsaturated group in the same molecule represented by Formulas XXXX and XXXXI include, for example, o-, m-, p-isopropenylphenyl cyanate; o-, m-, p-vinylphenyl cyanate; methyl-p-isopropenylphenyl cyanates; 3-chloro-4-isopropenylphenyl cyanate; o-, m-, p-propenylphenyl cyanate; o-, m-, p-allylphenyl cyanate; o-, m-, p-methallylphenyl cyanate and the like. Some of the alkenylphenol precursors to the alkenylphenyl cyanates represented by Formula XXXX, notably the vinylphenols, have a tendency to dimerize or oligomerize thus leading to poly(alkenylphenyl)cyanates. It is most preferred that the alkenylphenyl cyanate be substantially free of dimeric and/or oligomeric components, although it is operable to use an alkenylphenyl cyanate containing substantial (up to 90 percent by weight) dimeric and/or oligomeric components. A specific preparation of p-isopropenylphenyl cyanate is taught in Example 1 of U.S. Pat. No. 4,559,399 which ia incorporated herein by reference.

Compounds Containing Both a 1,2-Epoxide Group and a Polymerizable Ethylenically Unsaturated Group for Use in the Curable and Cured Compositions Suitable compounds which contain both a 1,2-epoxide group and a polymerizable ethylenically unsaturated group in the same molecule that can be used to prepare the polymerizable mixtures of the present invention include, for example, those represented by the following Formulas XXXXII or XXXXIII

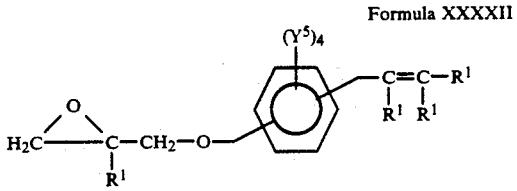

Formula XXXXII

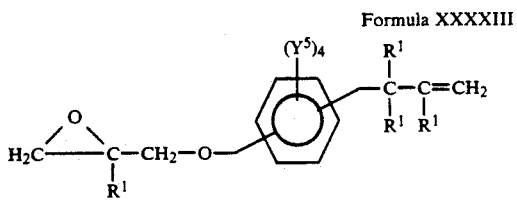

Formula XXXXIII wherein each Y$^5$ and R$^1$ are as hereinbefore defined.

Suitable compounds which contain a 1,2-epoxide group and a polymerizable ethylenically unsaturated group in the same molecule represented by Formulas XXXXII and XXXXIII include, for example, o-, m-, p-isopropenylphenyl glycidyl ether; o-, m-, p-vinylphenyl glycidyl ether; methyl-p-isopropenylphenyl glycidyl ethers; 3-chloro-4-isopropenylphenyl glycidyl ether; o-, m-, p-propenylphenyl glycidyl ether; o-, m-, p-allylphenyl glycidyl ether; o-, m-, p-methallylphenyl glycidyl ether and the like. Some of the alkenylphenol precursors to the alkenylphenyl glycidyl ethers represented by Formula XXXXII, notably the vinylphenols, have a tendency to dimerize or oligomerize thus leading to poly(alkenylphenyl)glycidyl ethers. It is most preferred that the alkenylphenyl glycidyl ether be substantially free of dimeric and/or oligomeric components, although it is operable to use an alkenylphenyl glycidyl ether containing substantial (up to 90 percent by weight) dimeric and/or oligomeric components. The compounds which contain a 1,2-epoxide group and a polymerizable ethylenically unsaturated group in the same molecule are prepared using the corresponding phenol containing a polymerizable ethylenically unsaturated group and the hereinbefore described chemistry used in the preparation of epoxy resins.

Compounds Containing Both a Maleimide Group and a Cyanate Group and no Rodlike Mesogenic Structures Suitable for Use in the Curable and Cured Compositions Suitable compounds which contain both a maleimide group and a cyanate group in the same molecule and do not contain rodlike mesogenic structure(s) that can be used to prepare the polymerizable mixtures of the present invention include, for example, those represented by the following Formulas XXXXIV or XXXXV

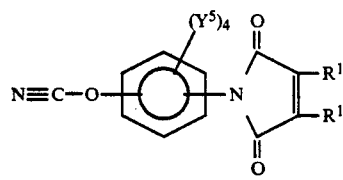

Formula XXXXIV

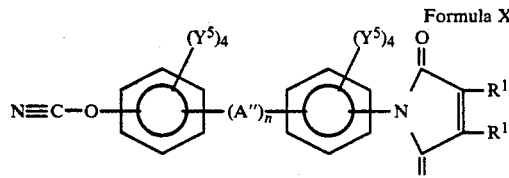

Formula XXXXV wherein each $Y^5$, $R^1$, $A''$ and n are as hereinbefore defined.

Suitable compounds which contain a maleimide group and a cyanate group in the same molecule and do not contain rodlike mesogenic structures represented by Formulas XXXXIV and XXXXV include, for example, 4-(1-(3-(2,5-dihydro-2,5-dioxo-1H-pyrrol-1-yl)phenyl)-1-methylethyl)phenyl cyanate; 4-(1-(4-(2,5-dihydro-2,5-dioxo-1H-pyrrol-1-yl)phenyl)-1-methylethyl)phenyl cyanate; 4-(1-(4-(2,5-dihydro-2,5-dioxo-1H-pyrrol-1-yl)phenyl)ethyl)phenyl cyanate; 4-(4-(2,5-dihydro-2,5-dioxo-1H-pyrrol-1-yl)phenoxy)phenyl cyanate; 4-((4-(2,5-dihydro-2,5-dioxo-1H-pyrrol-1-yl)phenyl)thio)phenyl cyanate; 4-(4-(2,5-dihydro-2,5-dioxo-1H-pyrrol-1-yl)benzoyl)phenyl cyanate; 4-((4-(2,5-dihydro-2,5-dioxo-1H-pyrrol-1-yl)phenyl)sulfonyl)phenyl cyanate; 4-(1-(4-(2,5-dihydro-3-methyl-2,5-dioxo-1H-pyrrol-1-yl)phenyl)-1-methylethyl)phenyl cyanate; 2,6-dibromo-4-(1-(3,5-dibromo-4-(2,5-dihydro-2,5-dioxo-1H-pyrrol-1-yl)phenyl)-1-methylethyl)phenylcyanate; 4-(2,5-dihydro-2,5-dioxo-1H-pyrrol-1-yl)phenyl cyanate; 3-(2,5-dihydro-2,5-dioxo-1H-pyrrol-1-yl)phenyl cyanate and the like. Preparation of compounds which contain a maleimide group and a cyanate group in the same molecule and do not contain rodlike mesogenic structures is taught in U.S. Pat. No. 4,683,276 which is incorporated herein by reference.

Compounds Containing One Cyanate or Cyanamide Group Per Molecule and One or More Rodlike Mesogenic Moieties which can be Employed in the Curable and Cured Compositions Suitable compounds which contain one or more rodlike mesogenic structure(s) and an average of one cyanate or cyanamide group per molecule that can be used to prepare the polymerizable mixtures of the present invention include, for example, those represented by the following Formulas XXXXVI, XXXXVII, XXXXVIII or XXXXIX

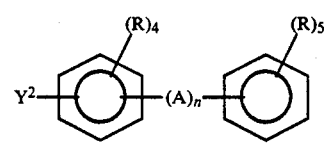

Formula XXXXVI

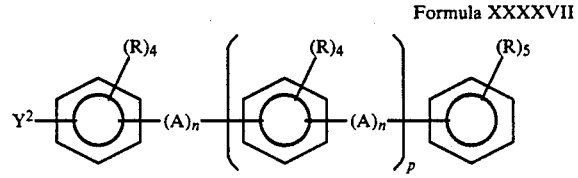

Formula XXXXVII

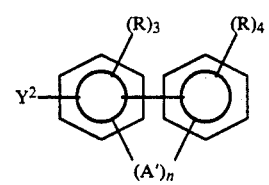

Formula XXXXVIII

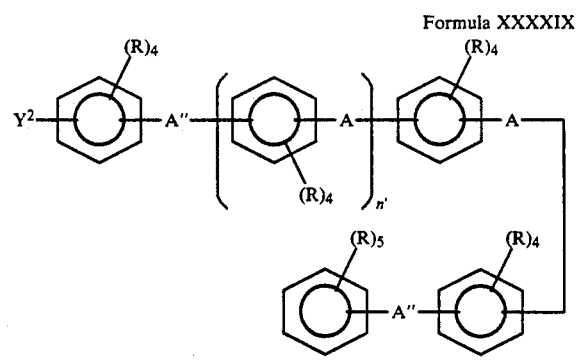

Formula XXXXIX wherein at least 80 percent of the —A— linkages in Formulas XXXXVI, XXXXVII and XXXXIX and the direct bond in Formula XXXXVIII and the $Y^2$ groups are in the para position with respect to each other and each A, A', A'', R, $Y^2$, p, n and n' are as hereinbefore defined.

Suitable compounds which contain one or more rodlike mesogenic structure(s) and an average of one cyanate or cyanamide group per molecule represented by Formulas XXXXVI, XXXXVII, XXXXVIII and XXXXIX include, for example, the cyanates of 4-hydroxystilbene, 4-hydroxy-4'-methoxystilbene, 4-hydroxy-4'-chlorostilbene, 4-hydroxy-4'-nitrostilbene, 4-hydroxy-4'-cyanostilbene, 4-hydroxy-alpha-methylstilbene, 4-hydroxychalcone, 1-(4-hydroxyphenyl)-2-phenylacetylene, 1-(4-hydroxyphenyl)-2-phenylazomethine, 4-hydroxyphenylazobenzene, 4-hydroxyphenylazoxybenzene, 4-(4-hydroxyphenoxy)diphenyl, 4-hydroxydiphenyl, 4-hydroxy-alpha-cyanostilbene, 4-hydroxy-alpha-ethylstilbene, 4-hydroxybenzanilide, 4-hydroxy-4'-methoxybenzanilide, 4-hydroxy-3,3',5,5'-tetramethyl-alpha-methylstilbene, N-methyl-4-hydroxybenzamide, N-phenyl-4-hydroxybenzamide, 4-hydroxy-3,3',5,5'-tetrabromo-alpha-methylstilbene, 4-hydroxyphenylbenzoate, phenyl-4-hydroxybenzoate, the cyanamides of 4-aminostilbene, 4-amino-alpha-methylstilbene, 4-aminobenzanilide, and the like. The compounds which contain one or more rodlike mesogenic structure(s) and an average of one cyanate or cyanamide group per molecule are prepared using the corresponding monophenol (monoamine) containing one or more rodlike mesogenic structure(s) and the hereinbefore described chemistry used in the preparation of polycyanates (polycyanamides).

Method for Forming the Mixtures of the Present Invention

The mixtures of the present invention can be prepared by directly combining one or more of the desired component(s) with one or more cyanate functional maleimides containing one or more rodlike mesogenic structures or by addition of one or more of the desired components to one or more of the cyanate functional maleimides containing one or more rodlike mesogenic structures in increments or stages. When a single component is to be added to one or more of the cyanate functional maleimides containing one or more rodlike mesogenic structures, said component may be prepolymerized (B-staged) or fully homopolymerized, prior to the addition. When two or more components are to be added to one or more of the cyanate functional maleimides containing one or more rodlike mesogenic structures, said components may be partially or totally copolymerized or reacted together, prior to the addition. Additionally, when two or more components are to be added to one or more of the cyanate functional maleimides containing one or more rodlike mesogenic structures, one component may be prepolymerized or fully homopolymerized in the presence of the other components, prior to the addition. It is understood that one or more catalysts or accelerators may be included where desired to facilitate the aforementioned copolymerization, prepolymerization, homopolymerization or reaction of one or more specific components.

The mixtures can comprise any amount of the compound or compounds containing at least one cyanate group, at least one maleimide group and at least one rodlike mesogenic moiety and the other component or components; however, the mixtures suitably contain from about 1 to about 99, more suitably from about 99 to about 40, most suitably from about 95 to about 70, percent by weight of the compound or compounds containing at least one cyanate group, at least one maleimide group and at least one rodlike mesogenic moiety and suitably from about 99 to about 1, more suitably from about 60 to about 1, most suitably from about 30 to about 5, percent by weight of the other component or components.

Polymerization (Curing) of the Polymerizable Mixtures

The mixtures of the present invention may be polymerized by heating from about 50° C. to about 400° C., preferably by heating from 100° C. to 250° C., optionally in the presence of one or more suitable catalysts. For the mixtures containing of one or more of the cyanate functional maleimides containing one or more rodlike mesogenic structures, whenever one or more polymaleimides, compounds containing one or more polymerizable ethylenically unsaturated group(s), compounds which simultaneously contain both a cyanate group or cyanamide group and a polymerizable ethylenically unsaturated group, compounds which simultaneously contain both a 1,2-epoxide group and a polymerizable ethylenically unsaturated group or compounds which simultaneously contain both a maleimide group and a cyanate group and no rodlike mesogenic structures are present, it is often desirable to utilize one or more free radical forming catalysts for the purpose of polymerizing all or a part of said unsaturated groups. Said free radical forming catalysts include the organic peroxides and hydroperoxides as well as the azo and diazo compounds. Preferred free radical forming catalysts include benzoylperoxide, t-butylhydroperoxide, t-butylperoxybenzoate, azobisisobutyronitrile, dicumylperoxide, di-tert-butylperoxide and cumene hydroperoxide. The quantity of catalyst used, if any, depends on the structure of the particular catalyst, the structure of the components used in the polymerizable mixture, the cure structure desired, the cure time, the cure temperature, and the like. Generally, catalyst concentrations of from about 0.001 to about 2 percent by weight are preferred. B-staging or prepolymerization of the mixtures of the present invention can be accomplished by using lower temperatures and/or shorter curing times. Curing of the thus formed B-staged (prepolymerized) mixture can then be accomplished at a later time or immediately following B-staging (prepolymerization) by increasing the temperature and/or curing time.

The polymerized (cured) mixtures possess a variety of curing structures which depend, in part, upon the amounts and types of individual components used to prepare said mixture, the sequence of component addition and procedure used to prepare said mixture, the amounts and types of catalysts, if any, employed, the reaction times and temperatures, and the like.

Mixtures of (A), one or more cyanate functional maleimides containing one or more rodlike mesogenic structures and no other moieties reactive with the cyanate or maleimide group, and (B-1), one or more polycyanates which do not contain rodlike mesogenic structures, and/or (B-3), one or more polymaleimides and/or prepolymers of any of the aforementioned types of compounds, polymerize to produce the aforementioned curing structures delineated for the (A), cyanate functional maleimides containing one or more rodlike mesogenic structures. It should be noted; however, that the relative mole ratio of cyanate groups to maleimide groups can influence the amounts of the various cure structures in the cured product. For example, a large excess of cyanate groups, provided by using an (B-1) aromatic polycyanate in the copolymerizable compositions increases the amount of the triazine cure structure in the cured product.

Mixtures of (A), one or more cyanate functional maleimides containing one or more rodlike mesogenic structures and no other moieties reactive with the cyanate or maleimide group, and (B-2), one or more epoxy resins, polymerize to produce a complex structure, including that derived from the copolymerization reaction if the cyanate group and the glycidyl ether group

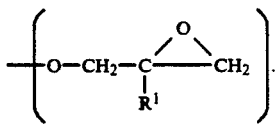

Additionally, curing structures derived from homopolymerization of the maleimide groups, homopolymerization of the cyanate groups (triazinei, as well as copolymerization of the cyanate and maleimide groups can be present.

Mixtures of (A), one or more cyanate functional maleimides containing one or more rodlike mesogenic structures and no other moieties reactive with the cyanate or maleimide group, and (B-4), one or more polyamines, polymerize to produce a complex structure including the iminocarbamic acid ester moiety derived from the copolymerization reaction of the cyanate group and the amine group, as well as the addition structure derived from the copolymerization reaction of the amine group and the maleimide unsaturation. Additionally, curing structures derived from homopolymerization of the maleimide groups, homopolymerization of the cyanate groups (triazine), as well as copolymerization of the cyanate and maleimide groups can be present.

Mixtures of (A), one or more cyanate functional maleimides containing one or more rodlike mesogenic structures and no other moieties reactive with the cyanate or maleimide group, and (B-5), one or more polyphenols, polymerize to produce a complex structure including the iminocarbonic acid ester moiety derived from the copolymerization reaction of the cyanate group and the phenolic hydroxyl group, as well as the addition structure derived from the copolymerization reaction of the phenolic hydroxyl group and the maleimide unsaturation. Additionally, curing structures derived from homopolymerization of the maleimide groups, homopolymerization of the cyanate groups (triazine), as well as copolymerization of the cyanate and maleimide groups can be present.

Mixtures of (A), one or more cyanate functional maleimides containing one or more rodlike mesogenic structures and no other moieties reactive with the cyanate or maleimide group, and (B-6), one or more polymerizable ethylenically unsaturated compounds, polymerize to produce a complex curing structure including structure derived from the copolymerization reaction of the maleimide group and the polymerizable ethylenically unsaturated group(s), as well as structure derived from the copolymerization reaction of the cyanate group and the polymerizable ethylenically unsaturated group(s). Additionally, curing structures derived from homopolymerization of the polymerizable ethylenically unsaturated groups, from homopolymerization of the maleimide groups, from homopolymerization of the cyanate groups (triazine), as well as copolymerization of the cyanate and maleimide groups can be present.

Mixtures of (A), one or more cyanate functional maleimides containing one or more rodlike mesogenic structures and no other moieties reactive with the cyanate or maleimide group, and (B-7), one or more compounds which simultaneously contain both a cyanate group and a polymerizable ethylenically unsaturated group, or (B-8), one or more compounds which simultaneously contain both a 1,2-epoxide group and a polymerizable ethylenically unsaturated group, or (B-9), one or more compounds which simultaneously contain both a maleimide group and a cyanate group and does not contain rodlike mesogenic structures, can polymerize to produce a complex variety of structures, including those previously mentioned for the various respective functional groups.

Mixtures of (A), one or more cyanate functional maleimides containing one or more rodlike mesogenic structures, and (B-10), one or more compounds which contain one or more rodlike mesogenic structures per and only one cyanate or cyanamide group per molecule, polymerize to produce the aforementioned curing structures delineated for the (A), cyanate functional maleimides containing one or more rodlike mesogenic structures; providing that no other moieties reactive with cyanate or maleimide groups are present in (A) or (B-10). Increasing the amount of the aforementioned cyanate compound containing an average of one cyanate group per molecule with respect to the amount of cyanate functional maleimide can be used as a convenient method for lowering the crosslink density of the thermoset product thereof.

Orientation of the Polymerized Product Containing Rodlike Mesogenic Structures

During processing and/or curing of the cyanate functional maleimides containing one or more rodlike mesogenic structures or the mixtures containing said cyanate functional maleimides, electric or magnetic fields or drawing and/or shear stresses can be applied for the purpose of orienting the rodlike mesogenic moieties contained or developed therein. As specific examples of these methods, Finkelmann, et. al., *Macromol. Chem.*, 180, 803–806 (March, 1979), which is incorporated herein by reference, induced orientation in an electric field, of thermotropic methacrylate copolymers containing mesogenic side chain groups decoupled from the main chain via flexible spacers. Orientation in a magnetic field of mesogenic side chain groups decoupled from the main chain via flexible spacers has been demonstrated by Roth and Kruecke, *Macromol. Chem.*, 187, 2655–2662 (November, 1986), which is incorporated herein by reference. Magnetic field induced orientation of mesogenic main chain containing polymers has been demonstrated by Moore, et. al., *ACS Polymeric Material Sciences and Engineering*, 52, 84–86 (April–May, 1985), which is incorporated herein by reference. Magnetic and electric field induced orientation of low molecular weight mesogenic compounds is discussed by W. Krigbaum in *Polymer Liquid Crystals*, pages 275–309 (1982), published by Academic Press, Inc., which is incorporated herein by reference. The use of shear to induce orientation is also discussed therein. When the curing is to be performed in an electric or magnetic field, it is frequently of value to conduct simple preliminary experiments that allow for balancing of cure kinetics versus induction of orientation under the particular experimental conditions being employed (i.e. catalyst(s) level being used, temperature used, inherent dielectric or diamagnetic susceptibility of the specific rodlike mesogenic structure(s) used, and the like). This is done recognizing the relatively greater ease of inducing orientation in low molecular weight materials versus polymeric materials containing mesogenic moieties.

In addition to orientation by electric or magnetic fields, the cyanate functional maleimides containing one or more rodlike mesogenic structures or mixtures containing said cyanate functional maleimides can be oriented by drawing and/or shear forces which are induced by flow through dies, orifices and mold gates. A general discussion of orientation of thermotropic liquid crystalline polymers by this method is given by S. K. Garg and S. Kenig in *High Modulus Polymers*, pages 71–103 (1988) published by Marcel Dekker, Inc., which is incorporated herein by reference. For the mesomorphic cyanate functional maleimides or mixtures containing said cyanate functional maleimides, this drawing and/or shear orientation can conveniently be produced by or during processing methods such as injection molding, extrusion, pultrusion, filament winding, filming and prepreging.

Other Components which can be Employed

The cyanate functional maleimides containing one or more rodlike mesogenic structures or mixtures containing said cyanate functional maleimides can be blended with other materials such as solvents or diluents, fillers including those comprising a liquid crystalline polymer, pigments, dyes, flow modifiers, thickeners, reinforcing agents, mold release agents, wetting agents, stabilizers, fire retardant agents, surfactants, low profile additives, shrinkage control agents, other resinous products, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based on the total weight of the composition.

Solvents or diluents which can be employed herein include, for example, hydrocarbons, ketones, aliphatic ethers, cyclic ethers, esters, chlorinated hydrocarbons, combinations thereof and the like. Particularly suitable solvents or diluents include, for example, toluene, xylenes, methylethyl ketone, methylisobutyl ketone, methylamyl ketone, chloroform, acetone, perchloroethylene, methylene chloride, tetrahydrofuran, 1,4-dioxane, ethyl acetate, butyl acetate, combinations thereof and the like.

The modifiers such as thickeners, flow modifiers, shrinkage control agents, low profile additives and the like can be suitably employed in amounts from about 0.05 to about 15, more suitably from about 0.1 to about 10, most suitably from about 0.1 to about 5 percent by weight based on the total weight of the composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include glass, ceramics, nylon, rayon, cotton, aramid, graphite, polyalkylene terephthlates, polyethylene, polypropylene, polyesters, carbon, boron, asbestos, combinations and hybrids thereof and the like.

Suitable fillers which can be employed herein include, for example, inorganic oxides, ceramic microspheres, plastic microspheres, glass microspheres, inorganic whiskers, calcium carbonate, graphite powder, sand, metal powders, combinations thereof and the like. The fillers can be employed in amounts from about 0.1 to about 95, more suitably from about 5 to about 80, most suitably from about 10 to about 50 percent by weight of the total composition.

Uses for the Compositions

The compositions of the present invention can be employed in the preparation of laminates, prepregs, composites, coatings, castings, pultruded products, filament wound products, films, molding and potting formulations, injection molded products, and the like.

The following examples are illustrative of the invention but are not to be construed as to limiting the scope thereof in any manner.

EXAMPLE 1

A. Synthesis of 4-Hydroxy-4'-nitrobenzanilide p-Hydroxybenzoic acid (59.05 grams, 0.4275 mole), sodium ethoxide catalyst (0.133 gram, 0.225% wt. of the p-hydroxybenzoic acid used) and N,N'-dimethylacetamide solvent (404 grams) are added to a reactor equipped with a reflux condenser and stirred under a nitrogen atmosphere at 80° C. p-Nitrophenylisocyanate (73.85 grams, 0.450 mole) is initially added in an aliquot of 25.00 grams, followed by 25.00 and 23–85 gram aliquots eleven then nine minutes later, respectively, and so as to maintain a 80° to 82° C. reaction temperature. After the last aliquot of p-nitrophenylisocyanate is added, heating of the reactor commenced and a 160° C. reaction temperature is achieved 24 minutes later. After three hours at the 160° C. reaction temperature, the reactor is cooled to 30° C. then the contents poured into one gallon of deionized water. A precipitated yellow powder is recovered via filtration of the aqueous slurry then dissolved into 1900 milliliters of boiling methanol and refluxed therein (65° C.). After cooling the methanol solution to 5° C. and maintaining therein for twelve hours, a first crop of pale yellow colored crystalline product is filtered off and dried at 110° C. under vacuum to a constant weight of 92.5 grams (79.6% isolated yield). No attempt was made to recover a second crop of crystalline product from the mother liquor. Fourier transform infrared spectrophotometric analysis of a nujol mull of a portion of the product on a sodium chloride plate revealed the presence of the expected secondary amide N—H stretching (solid state) at 3385 $cm^{-1}$ (sharp), the secondary amide carbonyl stretching (solid state) at 1655 $cm^{-1}$ (sharp), the hydroxyl group O—H stretching centered at 3232 $cm^{-1}$ (broad) and the conjugated nitro group absorbances at 1537 and 1339 $cm^{-1}$ (sharp). Proton magnetic resonance spectroscopy (250 MHz) further confirmed the product structure as -hydroxy-4'-nitrobenzanilide.

B. Synthesis of 4-Hydroxy-4'-aminobenzanilide

A portion (44.1 grams, 0.1708 mole) of 4-hydroxy-4'-nitrobenzanilide from A. above and ethanol (300 milliliters) are added to a 400 milliliter heavy walled glass bottle then sparged with nitrogen. After removal of air by nitrogen sparaing, Raney nickel catalyst (5.5 grams of a 75% wt. slurry in water at pH 10) is added to the slurry in the glass bottle which is then stoppered and multiply purged with hydrogen to replace the nitrogen atmosphere. The bottle is then placed on a shaking type agitator, and pressurized to 48 psig hydrogen. Shaking of the pressurized slurry at room temperature (25° C.) commences until 23.3 hours later, the hydrogen pressure reading indicates that 47 psig of hydrogen has been consumed. By the completion of the hydrogenation, the light yellow colored reactant slurry became a light pink tan colored product slurry. The product slurry is recovered, diluted into dimethylsulfoxide (300 milliliters) to provide a solution of product containing precipitated Raney nickel, then filtered through a medium porosity fritted glass funnel. The recovered dimethylsulfoxide product solution is rotary evaporated at 130° C. under vacuum to provide a powder product. The powder product is further dried at 120° C. under vacuum to a constant weight of 8.94 grams (99.88% isolated yield). Fourier transform infrared spectrophotometric analysis of a nujol mull of a portion of the product on a sodium chloride plate the presence of absorbances at 3376 (shoulder), 3351 (shoulder), 3316 (sharp) and 3282 (shoulder) cm$^{-1}$ due to secondary amide group N—H stretching (solid state), primary amine N—H group stretching and hydroxyl group O—H stretching; the secondary amide carbonyl stretching (solid state) at 1645 cm$^{-1}$ (sharp); and complete disappearance of the conjugated nitro group absorbances at 1537 and 1339 cm$^{-1}$ (sharp). Proton magnetic resonance spectroscopy (250 MHz) further confirmed the product structure as 4-hydroxy-4'aminobenzanilide.

C. Synthesis of Monomaleimide of 4-Hydroxy-4'-aminobenzanilide

A portion (38.50 grams, 0.1687 mole) of 4-hydroxy-4'-aminobenzanilide from B. above and dry acetic acid (800 milliliters) are added to a reactor and maintained under a nitrogen atmosphere with stirring. The stirred slurry is maintained at 25° C. while maleic anhydride (16.54 grams, 0.1687 mole) dissolved in dry acetic acid (100 milliliters) is added to the reactor. One minute after the addition, a maximum exotherm of 27° C. is achieved, then heating is started. Fifty nine minutes later, the slurry reaches a reaction temperature of 110° C. and is maintained therein for fourteen hours. The recovered product slurry is rotary evaporated at 80° C. under vacuum to provide a powder product. The powder product is then added to refluxing acetone (500 milliliters) and stirred therein as a slurry for five minutes. After cooling the acetone slurry to room temperature (25° C.), the first crop of light yellow green colored product is filtered off and dried at 80° C. under vacuum to a constant weight of 43.87 grams (84.38% isolated yield). No attempt was made to recover a second crop of product the mother liquor. Fourier transform infrared spectrophotometric analysis of a nujol mull of a portion of the product on a sodium chloride plate revealed the presence of absorbances at 3349 (sharp), 3289 (sharp) and 3087 (broad) cm$^{-1}$ due to secondary amide group N—H stretching (solid state), hydroxyl group O—H stretching; the secondary amide carbonyl stretching (solid state) at 1649 cm$^{-1}$ (sharp); and the maleimide carbonyl group stretching at 1702 cm$^{-1}$ (sharp). Proton magnetic resonance spectroscopy (250 MHz) further confirmed the product structure as the maleimide of 4-hydroxy-4'-aminobenzanilide.

D. Synthesis of the Cyanate of 4-Hydrox-,y-4'aminobenzanilide Maleimide

A portion (10–30 grams, 0.0334 mole) of the maleimide of 4-hydroxy-4'-aminobenzanilide from C. above, cyanogen bromide (3–72 grams, 0.0351 mole) and acetone (400 milliliters) are added to a reactor and maintained under a nitrogen atmosphere with stirring. The stirred slurry is cooled to −3° C., then triethylamine (3.40 grams, 0.0336 mole) is added to the reactor over a 10 minute period and so as to maintain the reaction temperature at −3 to −1° C. After completion of the triethylamine addition, the reactor is maintained at −3° to −1° C. for an additional 35 minutes followed by addition of the reactor contents to deionized water (2000 milliliters). After five minutes, the water and product mixture is multiply extracted with three 500 milliliter volumes of methylene chloride. The combined methylene chloride extract is washed with three 250 milliliter portions of deionized water, then dried over anhydrous sodium sulfate. The dry methylene chloride extract is filtered and solvent removed by rotary evaporation under a vacuum at 60° C. to provide a powder product. The remaining precipitated product not recovered by the methylene chloride extractions is directly filtered off then washed with two 250 milliliter portions of deionized water. After drying under vacuum at 65° C., a constant weight of 3.00 and 6.61 grams of light yellow colored powder is recovered from the methylene chloride extraction and the precipitation/filtration, respectively (86.31% isolated yield for the combined product). Fourier transform infrared spectrophotometric analysis of a nujol mull of a portion of the product on a sodium chloride plate revealed the presence of the expected secondary amide group N—H stretching (solid state) at 3348 cm$^{-1}$ (sharp), the secondary amide group carbonyl stretching (solid state) at 1659 cm$^{-1}$ (sharp), the maleimide group carbonyl stretching at 1706 cm$^{-1}$ (sharp) and the cyanate group absorbance at 2264 and 2242 cm$^{-1}$ (sharp) (the analysis was essentially identical for both product fractions). Proton magnetic resonance spectroscopy (250 MHz) further confirmed the product structure as the cyanate of 4-hydroxy-4'-aminobenzanilide maleimide.

E. Characterization of the Cyanate of 4-Hydroxy-4'-aminobenzanilide Maleimide for Liquid Crystallinity A portion (9.00 milligrams) of the cyanate of 4-hydroxy-4'-aminobenzanilide maleimide from D. above is analyzed by differential scanning calorimetry using a heating rate of 10° C. per minute under a stream of nitrogen flowing at 35 cubic centimeters per minute and the indicated temperature ranges. The following results were obtained:

| CYCLE DESIGNA-TION | OBSERVED TRANSITION TEMPERATURES (°C.) midpoint/range | EN-THALPY (J/g) | COMMENTS |
| --- | --- | --- | --- |
| First heating (30 to 375° C.) | 197/140–214 | 141.8 | Single peak exotherm |
|  | 269/219–366 | 169.1 | Single peak exotherm |

A repeat of the above first heating using a fresh sample (8.20 milligrams) and a range of 30° to 300° C. revealed a 273° C. midpoint for the second exothermic peak without a return to baseline by the 300° C. end of the analysis. A second heating of this second sample from 30° to 300° C. revealed only a slight and gradual exothermic shift of the baseline starting at 258° C.

The cured products are recovered from the differential scanning calorimetry as golden brown colored solids and are used to prepare nujol mulls. Fourier transform infrared spectrophotometric analysis of a film of the nujol mulls on a sodium chloride plate revealed that complete disappearance of the cyanate absorbance has occurred with retention of the secondary amide group carbonyl stretching (solid state) at 1653 cm$^{-1}$ (sharp) and the maleimide group carbonyl stretching at 1706 cm$^{-1}$ (sharp). The ratio of the amide group N—H absorbance to the amide group carbonyl group absorbance for both the cured product and the uncured product (from D. above) is found to be identical, hence substantial retention of the secondary amide group N—H stretching (3348 cm$^{-1}$) is implied. The appearance of a new absorbance at 1565 cm$^{-1}$ is observed in the cured product. The cured products from both of the differential scanning analysis gave essentially identical infrared spectrophotometric analysis.

Analysis of the maleimide cyanate via cross polarized light microscopy is completed using a microscope equipped with a programmable hot stage using a heating rate of 10° C. per minute and 35×magnification. The following results are obtained:

| CYCLE DESIGNATION | OBSERVED TRANSITION TEMPERATURES (°C.) | COMMENTS |
| --- | --- | --- |
| First heating | 25 | Immobile crystals. |
| | 196 | First fluidity noted as birefringent nematic droplets. |
| | 227 | Viscosity increasing, forms birefringent streaks in shear direction as sheared. |
| | 239 | Cures to a birefringent solid. |

COMPARATIVE EXPERIMENT A

1. Synthesis of the Cyanate of 3-Aminophenol Maleimide

A portion (11.45 grams, 0.0605 mole) of the maleimide of 3-aminophenol prepared using the method of U.S. Pat. No. 4,683,276, Example 1-A, cyanogen bromide (6.73 grams, 0.0636 mole) and acetone (300 milliliters) are added to a reactor and maintained under a nitrogen atmosphere with stirring. The stirred solution is cooled to −5° C., then triethylamine (6.16 grams, 0.0608 mole) is added to the reactor over a 10 minute period and so as to maintain the reaction temperature at −5° to −1° C. After completion of the triethylamine addition, the reactor is maintained at −3° to −1° C. for an additional 35 minutes followed by addition of the reactor contents to deionized water (1500 milliliters). After five minutes, the water and product mixture is multiply extracted with three 200 milliliter volumes of methylene chloride. The combined methylene chloride extract is washed with three 250 milliliter portions of deionized water, then dried over anhydrous sodium sulfate. The dry methylene chloride extract is filtered and solvent removed by rotary evaporation under a vacuum at 60° C. to provide a powder product. After drying under vacuum at 65° C., a constant weight of 11.08 grams light tan colored powder is recovered (85.47% isolated yield). Fourier transform infrared spectrophotometric analysis of a neat film of a portion of the product on a sodium chloride plate revealed the presence of the expected maleimide group carbonyl stretching at 1716 cm$^{-}$(sharp) and the cyanate group absorbance 2265 and 2234 cm$^{-1}$ (sharp). Proton magnetic resonance spectroscopy (250 MHz) further confirmed the product structure as the cyanate of 4-aminophenol maleimide.

2. Characterization of the Cyanate of 3-Aminophenol Maleimide for Liquid Crystallinity Results of the analysis of the cyanate of 3-aminophenol maleimide by differential scanning calorimetry are reported in U.S. Pat. No. 4,680,378, Comparative Experiment A. Analysis of the maleimide cyanate using cross polarized light microscopy as per the method of Example 1-E above demonstrated that the product became fluid upon heating without any birefringence. Shearing of the fluid produced no birefringence, and the product cured to a nonbirefringent solid.

EXAMPLE 2

A. Preparation and Curing of a Blend of the Cyanate of 4-Hydroxy-4'-aminobenzanilide Maleimide and Bisphenol A Dicyanate A portion (2.35 grams, 25% wt.) of the cyanate of 4-hydroxy-4'-aminobenzanilide maleimide from Example 1-D and bisphenol A dicyanate (7.05 grams, 75% wt.) are ground together to form a homogeneous powder blend. A portion (5.0 grams) of the resultant blend is heated to 125° C. to provide a homogeneous paste which is then catalyzed by vigorously mixing in cobalt naphthenate (6.0 percent active) (0.005 grams, 0.10% wt.) dissolved in methylene chloride (0.30 milliliter). The catalyzed blend is then placed in an oven which is preheated to 140° C. and held for ten minutes at this temperature. The molten blend is removed, degassed in a vacuum bell jar, then poured into the reservoir of an injection molder preheated to 140° C. Blend remaining after filling of the reservoir was poured into an aluminum dish and placed back into the 140° C. oven. After 10 minutes in the reservoir, the blend is injected through a 0.0625 inch square orifice into a mold preheated to 140° C. and having the following dimensions: 3.0 by 0.5 by 0.125 inches. The filled mold is immediately transferred to the 140° C. oven which also contains the blend in the aluminum dish. Heating of both the mold and the aluminum dish to 177° C. commences and this temperature is then maintained for 2 hours. The oven temperature is then increased to 200° C. and maintained therein for 2 hours followed by increasing to 240° C. After 2 hours at the 240° C. temperature, the oven is slowly cooled to room temperature (25° C.) then the casting is recovered from the mold and the film is recovered from the aluminum dish.

B. Dynamic Mechanical Analysis and Thermal Mechanical Analysis of the Cured Blend Dynamic mechanical analysis of the molded cured blend is completed using a heating rate of 5° C. per minute and a range of 30° C. to 300° C. The tensile storage modulus measured at 40°, 80°, 120°, 160° and 200° C. is reported in Table I. Thermal mechanical analysis of the film of the cured blend is completed with glass transition temperature and the mean linear thermal coefficient of expansion over the range of 30° C. to Tg evaluated. In this analysis, a constant probe force of 0.1 Newtons and a heating rate of 10° C. per minute is used over a range of 25° C. to 330° C. The results are reported in Table I.

COMPARATIVE EXPERIMENT B

1. Preparation and Curing of a Blend of the Cyanate of 3-Aminophenol Maleimide and Bisphenol A Dicyanate A portion (9.40 grams, 25% wt.) of the cyanate of 3-aminophenol maleimide from Comparative Experiment A-1 and bisphenol A dicyanate (28.20 grams, 75% wt.) are ground together to form a homogeneous powder blend. A portion (5.0 grams) of the resultant blend is heated to 125° C. to provide a homogeneous paste which is then catalyzed by vigorously mixing in cobalt naphthenate (6.0 percent active) (0.005 grams, 0.10% wt.) dissolved in methylene chloride (0–30 milliliter). The catalyzed blend is then used to prepare a molded test piece and a film using the method of Example 2-A.

2. Dynamic Mechanical Analysis and Thermal Mechanical Analysis of the Cured Blend Dynamic mechanical analysis of the molded cured blend is completed using the method of Example 2-B. Thermal mechanical analysis of the film of the cured blend is completed with glass transition temperature and the mean linear thermal coefficient of expansion over the range of 30° C. to Tg evaluated using the method of Example 2. The results are reported in Table I.

TABLE I

| | DESIGNATION OF SAMPLE | |
|---|---|---|
| | EXAMPLE 2 | COMP. EXPT. B* |
| Dynamic Mechanical Analysis: Tensile Storage Modulus (GPa) | | |
| 40° C. | 1.430 | 0.877 |
| 80° C. | 1.284 | 0.826 |
| 120° C. | 1.220 | 0.770 |
| 160° C. | 1.146 | 0.726 |
| 200° C. | 1.022 | 0.634 |
| Thermal Mechanical Analysis: | | |
| Tg (°C.) | 228.5 | 202.8 |
| Mean linear Coefficient of Thermal Expansion (ppm/°K.) | 48 | 63 |

*Not an example of the present invention.

EXAMPLE 3

A. Synthesis of a-p-Nitrophenyl-p-acetoxycinnamic Acid p-Nitrophenylacetic acid (94.02 grams, 0.519 mole) and 1.038 N sodium hydroxide solution (500 mL) are added to a 1,000 mL beaker and heated with stirring to 60° C. The resultant solution is rotary evaporated under vacuum until final conditions of 110° C. and 1 mm Hg are achieved and maintained for 30 minutes. A portion (101.6 grams, 0.50 mole) of the resultant dry white carboxylic acid sodium salt, p-hydroxybenzaldehyde (61.06 grams, 0.50 mole) and acetic anhydride (250 grams) are added to a reactor equipped with a reflux condenser and stirred under a nitrogen atmosphere at a 147° C. reflux. Refluxing continued over the next twenty hours at which time the temperature has increased to 159° C. At this time, the reactor is cooled to 100° C. and ethanol (300 mL) and water (50 mL) are added. The resultant slurry is boiled at 89° C. for one hour followed by cooling to 50° C. and filtration. The filtrate is added to deionized water (1500 mL) and the resultant precipitate recovered by filtration. The precipitate is exhaustively extracted with deionized water saturated with sodium carbonate. The combined extracts are filtered then neutralized with concentrated hydrochloric acid inducing formation of a precipitate. The precipitate is recovered by filtration then dried at 50° C. in a forced air convection type oven. The dry powder is added to a beaker along with carbon tetrachloride (200 mL) then stirred with heating to a boil. Acetic acid (40 mL) is added to the boiling slurry then heating back to a boil resumed. After boiling is achieved, the slurry is maintained at 4° C. for 15 hours. The precipitate is recovered by filtration and dried at 70° C. under a vacuum of 5 mm Hg to a constant weight of 38.55 grams of brilliant light yellow colored crystalline powder.

B. Synthesis of 4-Nitro-4'-hydroxystilbene

A portion (36.75 grams) of a-p-nitrophenyl-p-acetoxycinnamic acid from A. above, ethanol (300 mL) and concentrated hydrochloric acid (300 mL) are added to a reactor equipped with a reflux condenser and stirred under a nitrogen atmosphere. Heating commenced and a reflux is achieved at 93° C. Refluxing continued over the next 262 minutes at which time the temperature has increased to 95° C. At this time, the contents of the reactor are poured into deionized water (one liter) and the resultant precipitate recovered by filtration. The wet filter cake is washed with two portions (500 mL) of deionized water then dissolved in stirred ethanol (750 mL) maintained at 82° C. The resultant solution is maintained at 4° C. for 15 hours. The precipitate is recovered by filtration and dried at 75° C. under a vacuum of 2 mm Hg to a constant weight of 22.70 grams of light orange colored crystalline needles. Fourier transform infrared spectrophotometric analysis of a potassium chloride pellet of a portion of the product revealed the presence of the expected hydroxyl group O—H stretching centered at 3422 cm$^{-1}$ (broad), conjugated nitro group absorbances at 1516 and 1337 (1317 shoulder) cm$^{-1}$ (sharp) and the ethylene C-H out-of-plane deformation at 972 cm$^{-1}$.

C. Synthesis of 4-Hydroxy-4'-aminostilbene

A portion (20.9 grams, 0.0866 mole) of 4-nitro-4'-hydroxystilbene from B. above and ethanol (300 mL) are added to a 400 milliliter heavy walled glass bottle then sparged with nitrogen. After removal of air by nitrogen sparging, Raney nickel catalyst (2.5 grams of a 50% wt. slurry in water at pH 10) is washed one time with ethanol, then added to the slurry in the glass bottle which is then stoppered and multiply purged with hydrogen to replace the nitrogen atmosphere. The bottle is then placed on a shaking type agitator, and pressurized to 46.5 psig (320.6 kPa) hydrogen. Shaking of the pressurized slurry at room temperature (25° C.) commences until 28.5 hours later, the hydrogen pressure reading indicates that 19.6 psig (135.1 kPa) of hydrogen has been consumed. The product slurry is recovered, diluted into dimethylsulfoxide (150 grams) to provide a solution of product containing precipitated Raney nickel, then filtered through a medium porosity fritted glass funnel. The recovered dimethylsulfoxide product solution is rotary evaporated at 130° C. under vacuum to provide a powder product. The powder product is further dried at 100° C. under vacuum of 2 mm Hg to a constant weight of 18.17 grams (99.25% isolated yield) of orange brown colored powder. Fourier transform infrared spectrophotometric analysis of a potassium chloride pellet of a portion of the product revealed the presence of absorbances at 3363 (sharp) and 3289 cm$^{-1}$ (sharp) due to primary amine N—H group stretching and hydroxyl group O—H stretching, complete disappearance of the conjugated nitro group absorbances at 1516 and 1337 (1317 shoulder) cm$^{-1}$ (sharp) and the ethylene C—H out-of-plane deformation at 965 cm$^{-1}$. Nuclear magnetic resonance spectroscopy confirmed the integrity of the stilbene ethylenic unsaturated structure.

D. Synthesis of Monomaleimide of 4-Hydroxy-4'-aminostilbene

A portion (17.63 grams, 0.0835 mole) of 4-hydroxy-4'-aminostilbene from C. above, dry acetic acid (500 mL) and maleic anhydride (8.18 grams, 0.0835 mole) dissolved in acetic acid (100 grams) are added to a reactor and maintained under a nitrogen atmosphere with stirring. Heating commenced and the slurry reaches a reaction temperature of 110° C. and is maintained thereat for fourteen hours. The recovered product slurry is rotary evaporated at 70° C. under vacuum of 1 mm Hg to provide a powder product. The powder product is then added to refluxing acetone (75 mL) and stirred therein as a slurry for five minutes. After cooling the acetone slurry to room temperature (24° C.), the first crop of golden yellow colored product is filtered off and is dried at 70° C. under vacuum to a constant weight of 19.14 grams (78.73% isolated yield). No attempt is made to recover a second crop of product from the mother liquor. Fourier transform infrared spectrophotometric analysis of a potassium chloride pellet of a portion of the product revealed the presence of absorbances centered at 3442 cm$^{-1}$ (broad) due to the hydroxyl group O—H stretching, the maleimide carbonyl group stretching at 1702 cm$^{-1}$ (sharp) (1775 cm$^{-1}$ shoulder) and the ethylene C-H out-of-plane deformation at 965 cm$^{-1}$. Differential scanning calorimetry of a portion (10.95 milligrams) of the product using a heating rate of 10° C. per minute under a stream of nitrogen flowing at 35 cubic centimeters per minute and a temperature range of 30° to 375° C. revealed a single exotherm with an onset temperature of 196° C., midpoint temperature of 254° C., endpoint temperature of 369° C. and an enthalpy of 218 J/g.

E. Synthesis of the Cyanate of 4-Hydroxy-4'-aminostilbene Maleimide

A portion (14.56 grams, 0.05 mole) of the maleimide of 4-hydroxy-4'-aminostilbene from D. above, cyanogen bromide (5.56 grams, 0.0525 mole) and acetone (1600 mL) are added to a reactor and maintained under a nitrogen atmosphere with stirring. The stirred slurry is cooled to −2° C., then triethylamine (5.09 grams, 0.0503 mole) is added to the reactor over a 5 minute period and so as to maintain the reaction temperature at −2° to −1° C. After completion of the triethylamine addition, the reactor is maintained at −2° to 0° C. for an additional 40 minutes followed by addition of the reactor contents to deionized water (3000 mL). After five minutes, the precipitated product is directly filtered off then washed with three 250 mL portions of deionized water. After drying under vacuum of 2 mm Hg at 65° C., a constant weight of 15.3 grams of yellow colored powder is recovered (96.74% isolated yield). Fourier transform infrared spectrophotometric analysis of a potassium chloride pellet of a portion of the product revealed the presence of the maleimide group carbonyl stretching 1716 cm$^{-1}$ (sharp) (1775 cm$^{-1}$ shoulder) and the cyanate group absorbance at 2267 and 2234 cm$^{-1}$ (sharp) and the ethylene C—H out-of-plane deformation at 965 cm$^{-1}$.

F. Characterization of the Cyanate of 4-Hydroxy-4'-aminostilbene Maleimide for Liquid Crystallinity A portion (10.43 milligrams) of the cyanate of 4-hydroxy-4'-aminostilbene maleimide from E. above is analyzed by differential scanning calorimetry using a heating rate of 10° C. per minute under a stream of nitrogen flowing at 35 cubic centimeters per minute and the indicated temperature ranges. The following results are obtained:

| Cycle Designation | Observed Transition Temperatures (°C.) midpoint/range | Enthalpy (J/g) | Comments |
|---|---|---|---|
| First Heating (30 to 375° C.) | 168 and 295/79–371 | 510.7 | Pair of exotherms which merge. |

The cured product is recovered from the differential scanning calorimetry as a brown colored solid and is used to prepare a potassium chloride pellet. Fourier transform infrared spectrophotometric analysis revealed that complete disappearance of the cyanate absorbance has occurred with retention of the maleimide group carbonyl stretching at 1702 cm$^{-1}$ (sharp) 1769 cm$^{-1}$ shoulder) and the ethylene C—H out-of-plane deformation at 965 cm$^{-1}$. The appearance of a new absorbance at 1565 cm$^{-1}$ is observed in the cured product.

Analysis of the maleimide cyanate via crosspolarized light microscopy is completed using a microscope equipped with a programmable hot stage using a heating rate of 10° C. per minute and 35×magnification. The following results are obtained:

| Cycle Designation | Observed Transition Temperatures (°C.) midpoint/range | Comments |
|---|---|---|
| First Heating | 25 | Immobile crystals. |
| | 144 | First fluidity noted with birefringent nematic texture when compressed between slide and coverslip. |
| | 154 | Birefringent nematic fluid. |
| | 202 | Birefringent nematic fluid with increasing viscosity. |
| | 212 | Cures to a birefringent solid. |

EXAMPLE 4

Preparation of a Cured Casting of the Cyanate of 4-Hydroxy-4'-aminostilbene Maleimide A portion (1.016 grams) of the cyanate of 4-hydroxy-4'-aminostilbene maleimide from Example 3-E is placed in an aluminum pan. The aluminum pan is then placed in a forced air convection type oven which has been preheated to 180° C. Within the first five minutes in the oven, melt is observed followed by thermosetting. After two hours at 180° C., the oven temperature is increased 20° C. every two hours to a final temperature of 240° C. After four hours at the 240° C. temperature, the oven is allowed to slowly cool to room temperature (24° C.). Once at room temperature, the casting is removed from the pan and examined by crosspolarized light microscopy at 70×magnification. A high level of birefringence is observed in the cured product. A portion (25 milligrams) of the casting is analyzed by differential scanning calorimetry using a heating rate of 10° C. per minute under a stream of nitrogen flowing at 35 cubic centimeters per minute and a temperature range of 30° to 300° C. In this analysis, no glass transition temperature is observed to 270° C. where a rise in heat flow occurs.

What is claimed is:

1. A compound containing at least one cyanate group, at least one maleimide group and at least one rodlike mesogenic moiety, wherein at least 80 percent of said cyanate groups and maleimide groups are in the para position with respect to the rodlike mesogenic moiety which is represented by the following Formulas I, II, III or IV

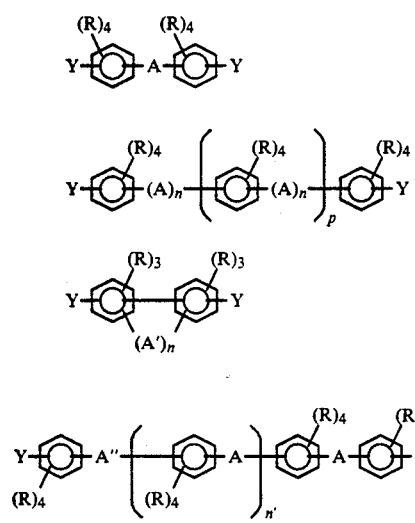

Formula I

Formula II

Formula III

Formula IV wherein at least about 80 percent of the —A— linkages in Formulas I, II and IV and the direct bond in Formula III and the Y groups are in the para position with respect to each other; one Y group is a cyanate, —O—C≡N, group and the other Y group is a maleimide group represented by the formula each A is independently —CR$^1$=CR$^1$—, —C≡C—, —N=N—, —CR$^1$=N—, —O—CO—, —NR$^1$—CO—, —NR$^1$=N—N=CR$^1$—, —CR$^1$=CR$^1$—CO—, —CO—O—, —CO—NR$^1$—, —CO—CR$^1$=CR$^1$—, —CR$^1$=CR$^1$—O—CO—(CH$_2$)$_{n'}$—, —N=CR$^1$—, —(CH$_2$)$_{n'}$—CO—O—CR$^1$=CR$^1$—, —CR$^1$=C-R$^1$—O—CO—, —CO—O—CR$^1$=CR$^1$—, —CO—O—N=CR$^1$—, —CR$^1$=N—O—CO—, —CR$^1$=CR$^1$—CO—O—, —CO—S—, —O—CO—CR$^1$=CR$^1$—, —CR$^1$=CR$^1$—CO—O—(CH$_2$)$_{n'}$—, —S—CO—, —(CH$_2$)$_{n'}$—O—CO—CR$^1$=CR$^1$—, —CHR$^1$—CHR$^1$—CO—O—, —O—CO—CHR$^1$—CHR$^1$—, —C≡C—C≡C—, —CR$^1$=C-R$^1$—CR$^1$=CR$^1$—, —CO—NR$^1$—NR$^1$—CO—,

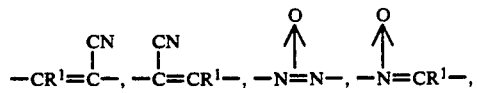

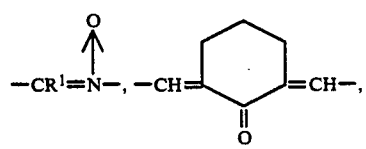

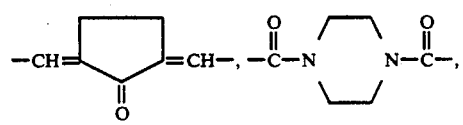

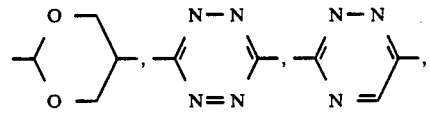

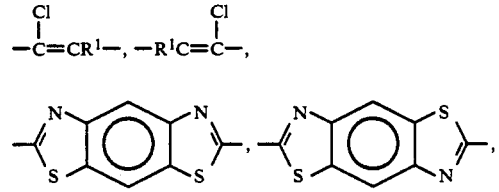

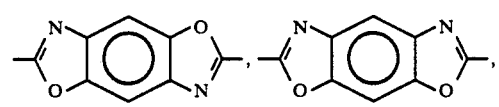

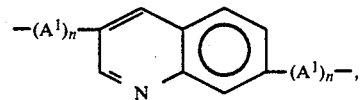

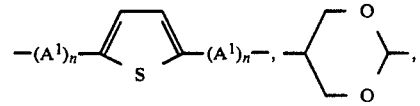

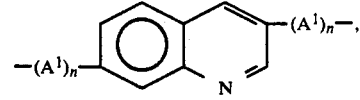

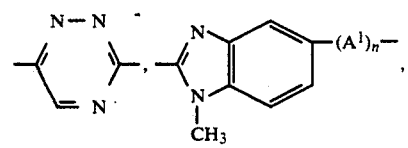

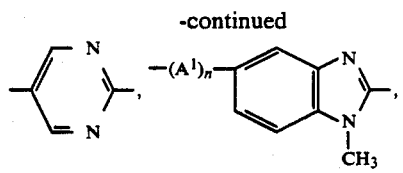

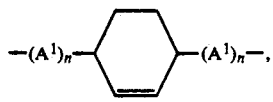

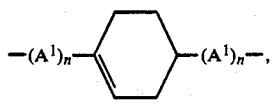

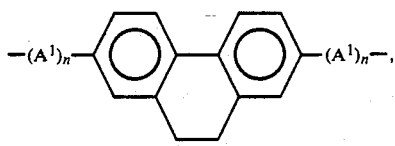

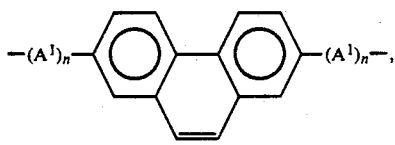

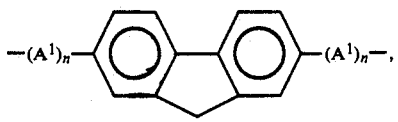

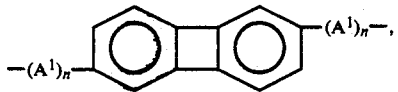

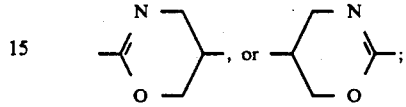

A' is a divalent hydrocarbyl group having from 1 to about 10 carbon atoms; each A" is independently an alkylene group having from 1 to about 10 carbon atoms carbon atoms, a direct bond, —O—, —CO—, —S—, —S—S—, —SO—, —SO$_2$— or —O—CO—O—; each A$^1$ is independently a —CO—, —O—CO—, —CO—O—, —CO—NR$^1$—, or —NR$^1$—CO— group; each R is independently hydrogen or a hydrocarbyl or hydrocarbyloxy group having from 1 to about 10 carbon atoms, a halogen atom, a nitro group, a nitrile group, a phenyl group or a —CO—R$^1$ group; each R$^1$ is independently hydrogen or a hydrocarbyl group having 1 to about 3 carbon atoms; n has a value of zero or 1; n' has an average value from zero to about 6; and p has an average value from 1 to about 30; with the proviso that any of the aromatic rings can, if desired, contain a nitrogen, oxygen or sulfur heteroatom.

2. A compound of claim 1 wherein A' has from 1 to about 4 carbon atoms; when A" is an alkylene group, it has from 1 to about 4 carbon atoms; each R is independently hydrogen or a hydrocarbyl group having from 1 to about 4 carbon atoms, chlorine or bromine; n' has an average value from zero to about 3; and p has an average value from 1 to about 3.

3. A compound of claim 1 selected from the group consisting of

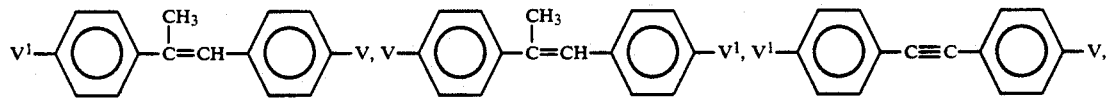

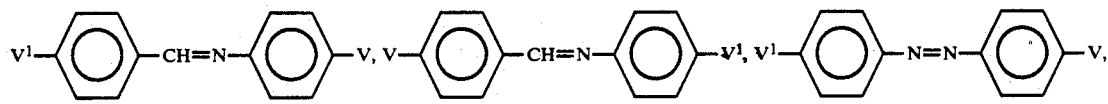

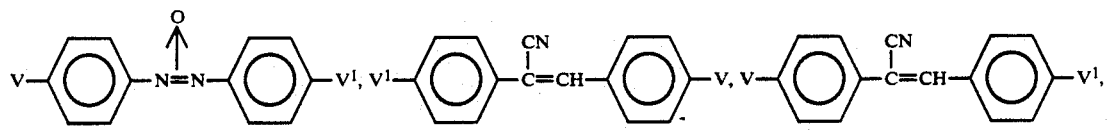

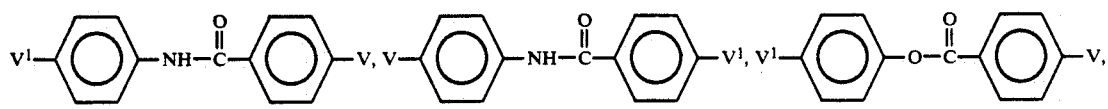

-continued
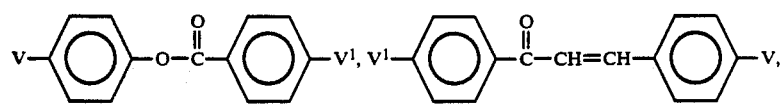
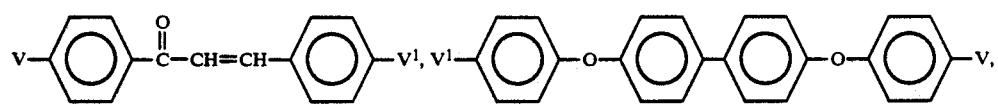
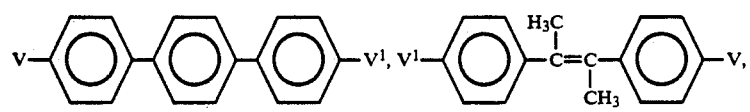
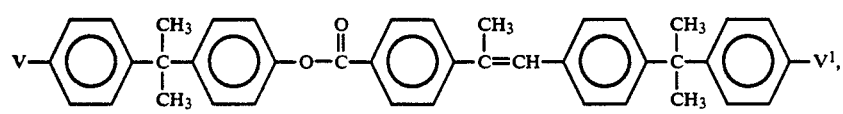
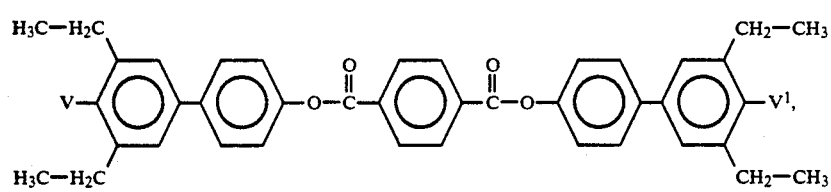
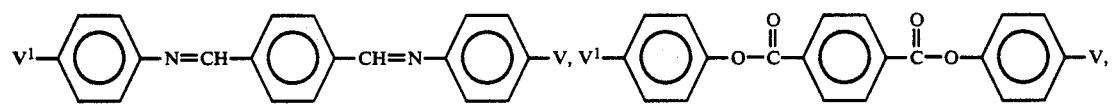
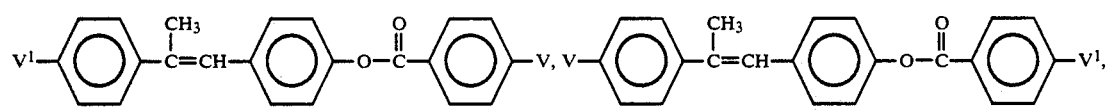
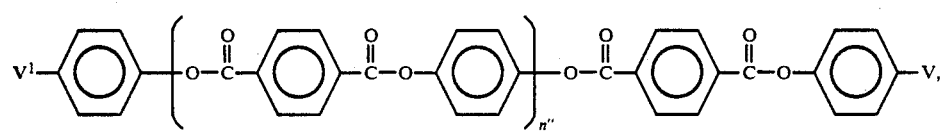
wherein n'' has a value from 1 to about 10,
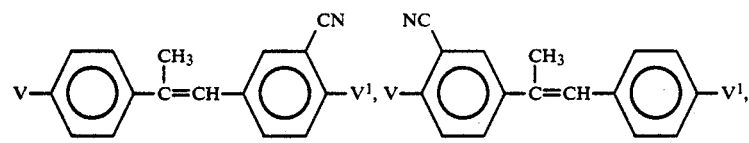
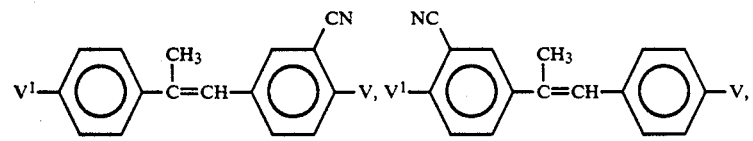
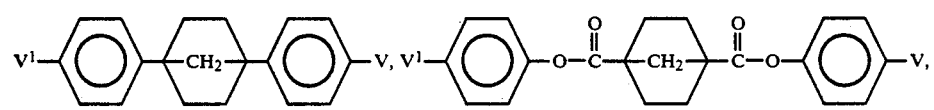
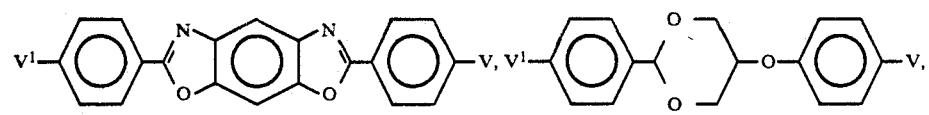

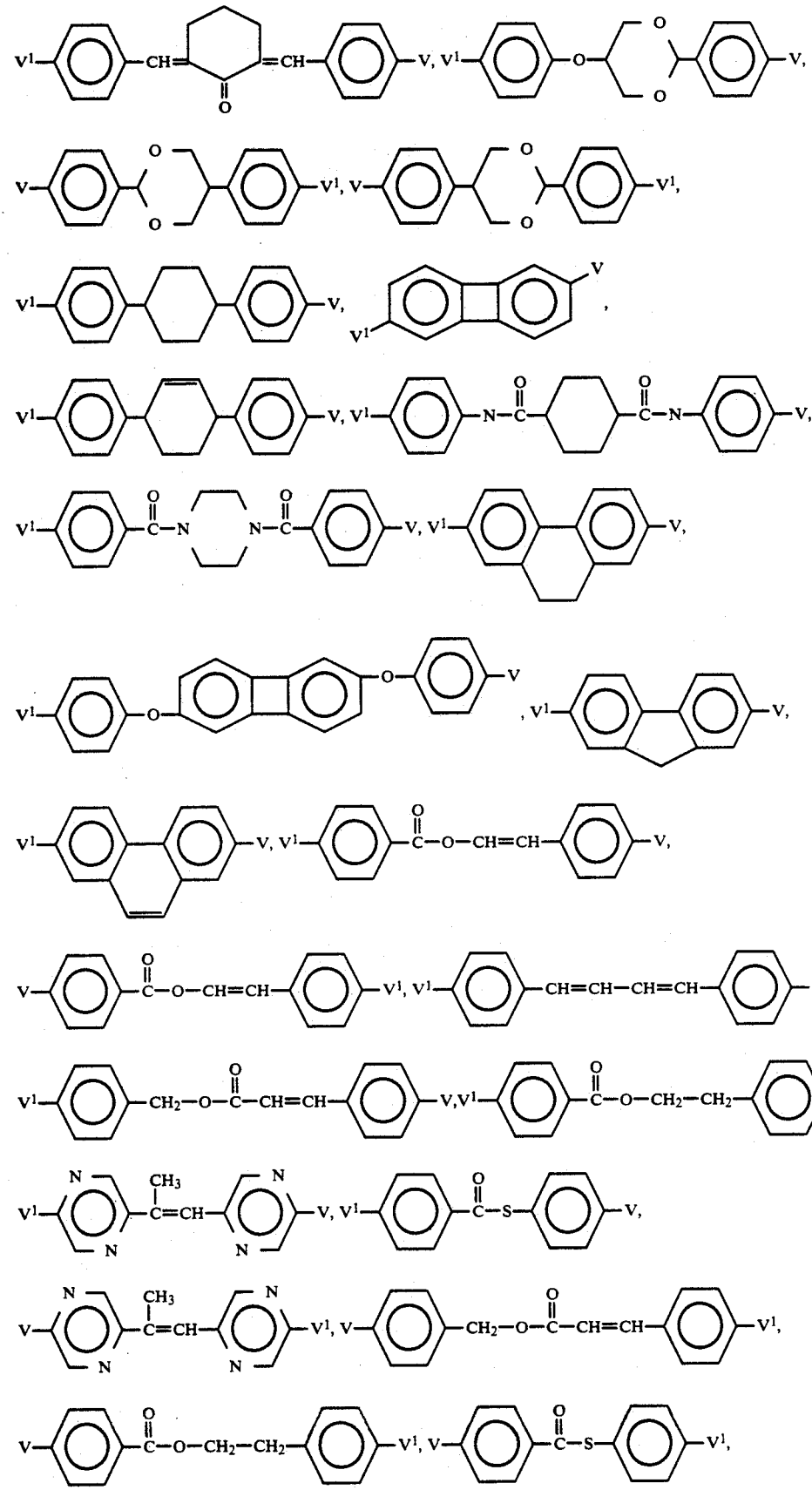

where $V^1$ is a maleimide group represented by the formula
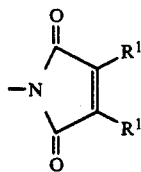
and V is a cyanate group, —O—C≡N, and where $R^1$ is independently hydrogen or a hydrocarbyl group having 1 to about 3 carbon atoms.
* * * * *

UNITED STATES PATENT AND TRADEMARK OFFICE
CERTIFICATE OF CORRECTION

PATENT NO.  : 5,248,757
DATED       : September 28, 1993
INVENTOR(S) : Robert E. Hefner, Jr. and Jimmy D. Earls It is certified that error appears in the above-identified patent and that said Letters Patent is hereby corrected as shown below:

In claim 1, line 62, column 51, "—NR¹" should read as ——CR¹——.

Signed and Sealed this

Twenty-sixth Day of July, 1994

Attest:

Attesting Officer

BRUCE LEHMAN

Commissioner of Patents and Trademarks